(12) United States Patent
Doyle

(10) Patent No.: US 7,044,441 B2
(45) Date of Patent: May 16, 2006

(54) VALVED MALE LUER CONNECTOR HAVING SEQUENTIAL VALVE TIMING

(75) Inventor: Mark C. Doyle, San Diego, CA (US)

(73) Assignee: Cardinal Health 303, Inc., San Diego, CA (US)

( * ) Notice: Subject to any disclaimer, the term of this patent is extended or adjusted under 35 U.S.C. 154(b) by 0 days.

(21) Appl. No.: 11/010,096

(22) Filed: Dec. 10, 2004

(65) Prior Publication Data

US 2005/0087715 A1  Apr. 28, 2005

Related U.S. Application Data

(63) Continuation-in-part of application No. 10/389,652, filed on Mar. 13, 2003, now Pat. No. 6,964,406, which is a continuation-in-part of application No. 09/927,109, filed on Aug. 10, 2001, now Pat. No. 6,745,998.

(51) Int. Cl.
*F16K 51/00* (2006.01)
*F16L 29/00* (2006.01)
*F16L 37/28* (2006.01)

(52) U.S. Cl. ............................. 251/149.6; 251/149.3; 251/149.4; 604/241

(58) Field of Classification Search ............ 251/149.1, 251/149.3, 149.4, 149.6; 604/167.02, 167.03, 604/167.04, 200, 201, 246, 249, 905, 241
See application file for complete search history.

(56) References Cited

U.S. PATENT DOCUMENTS

| | | |
|---|---|---|
| 2,931,668 A | 4/1960 | Baley |
| 2,968,497 A | 1/1961 | Treleman |
| 4,233,982 A | 11/1980 | Bauer et al. |
| 4,245,635 A | 1/1981 | Kontos |
| 4,379,458 A | 4/1983 | Bauer et al. |
| 4,862,913 A | 9/1989 | Wildfang |
| 5,065,783 A | 11/1991 | Ogle, II |
| 5,098,385 A | 3/1992 | Walsh |
| 5,203,775 A | 4/1993 | Frank et al. |
| 5,211,634 A | 5/1993 | Vaillancourt |

(Continued)

FOREIGN PATENT DOCUMENTS

WO   WO 03/013646 A2   2/2003

*Primary Examiner*—Edward K. Look
*Assistant Examiner*—John K. Fristoe, Jr.
(74) *Attorney, Agent, or Firm*—Fulwider Patton LLP

(57) ABSTRACT

A male Luer connector that attaches to a standard female Luer connector to open a medical fluid flow channel between the two connectors. The male connector has two internal valves and a vacuum-generating structure. The two valves and the vacuum-generating structure are configured to draw back into the male connector any fluid residing on the interface between the male and female connectors during their disengagement from one another and to then seal the distal tip of the male connector. One valve is located at the proximal end of the male connector while another is located at the distal, interface end of the male connector. Both valves are opened by an actuator plug that is moved to open and close the valves by contact with the front surface of the female connector. A resilient member biases the male valves to the closed position and includes a variable internal volume that creates the partial vacuum upon disengagement of the male and female connectors. The male valves are timed to a particular sequence with the closing of an internal female connector valve so that the partial vacuum generated by the male connector will have the most fluid drawback effect.

21 Claims, 15 Drawing Sheets

U.S. PATENT DOCUMENTS

| | | |
|---|---|---|
| 5,334,159 A | 8/1994 | Turkel |
| 5,380,306 A | 1/1995 | Brinon |
| 5,397,314 A | 3/1995 | Farley et al. |
| 5,405,323 A | 4/1995 | Rogers et al. |
| 5,405,333 A | 4/1995 | Richmond |
| 5,492,147 A | 2/1996 | Challender et al. |
| 5,514,117 A | 5/1996 | Lynn |
| 5,520,665 A | 5/1996 | Fleetwood |
| 5,540,661 A | 7/1996 | Tomisaka et al. |
| 5,549,566 A | 8/1996 | Elias et al. |
| 5,575,769 A | 11/1996 | Vaillancourt |
| 5,578,059 A | 11/1996 | Patzer |
| 5,584,819 A | 12/1996 | Kopfer |
| 5,645,538 A | 7/1997 | Richmond |
| 5,676,346 A | 10/1997 | Leinsing |
| 5,738,144 A | 4/1998 | Rogers |
| RE35,841 E | 7/1998 | Frank et al. |
| 5,782,816 A | 7/1998 | Werschmidt et al. |
| 5,806,831 A | 9/1998 | Paradis |
| 5,839,715 A | 11/1998 | Leinsing |
| 5,848,994 A | 12/1998 | Richmond |
| 6,068,011 A | 5/2000 | Paradis |
| 6,079,432 A | 6/2000 | Paradis |
| 6,106,502 A | 8/2000 | Richmond |
| 6,113,068 A | 9/2000 | Ryan |
| 6,142,446 A | 11/2000 | Leinsing |
| 6,206,860 B1 | 3/2001 | Richmond |
| 6,299,132 B1 | 10/2001 | Weinheimer et al. |
| 6,485,472 B1 | 11/2002 | Richmond |
| 2003/0060779 A1 | 3/2003 | Richmond |

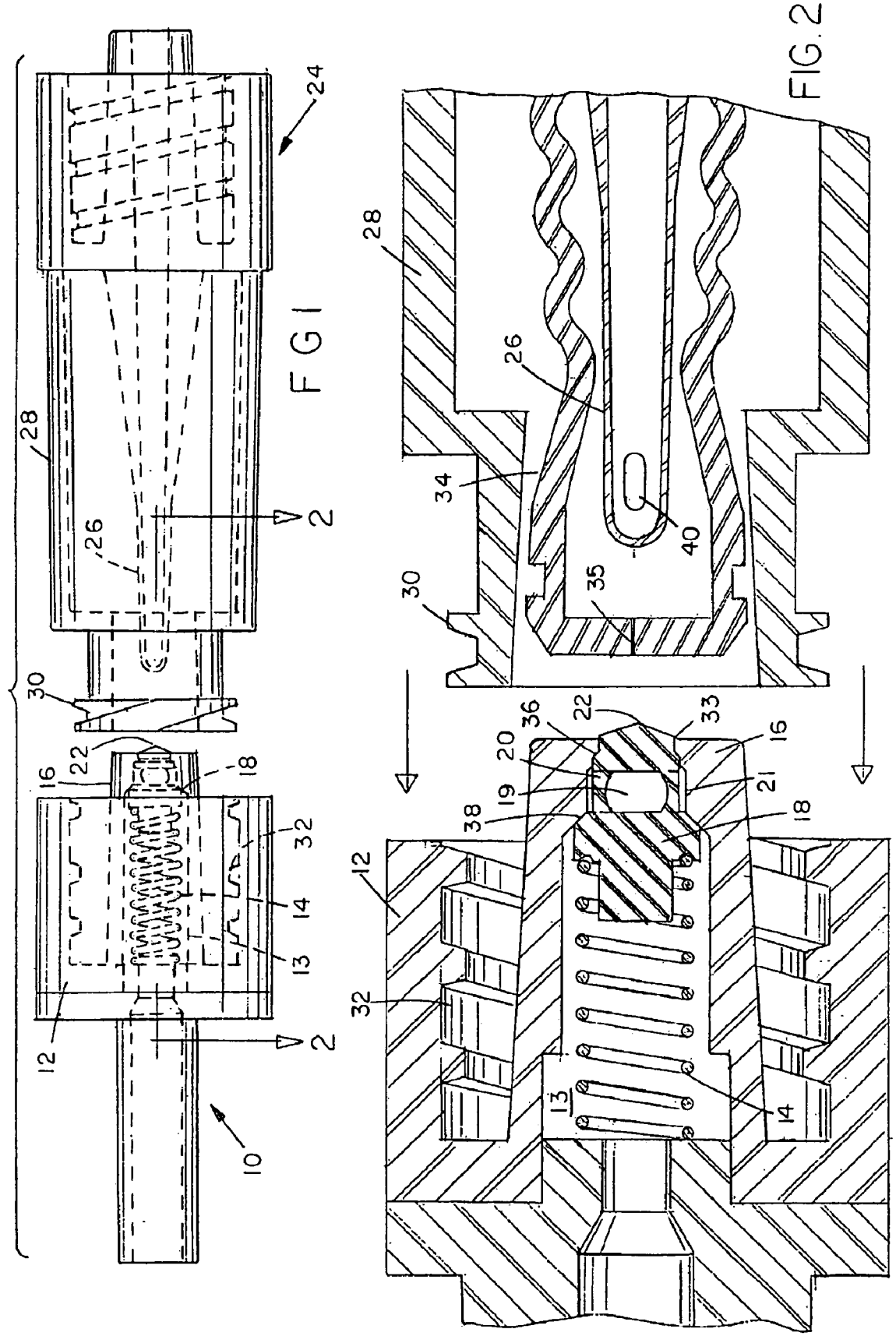

1

VALVED MALE LUER CONNECTOR HAVING SEQUENTIAL VALVE TIMING

CROSS REFERENCES TO OTHER APPLICATIONS

This application is a continuation-in-part of application Ser. No. 10/389,652 filed Mar. 13, 2003 now U.S. Pat. No. 6,964,406, having a publication No. of 2003/0136932 A1, which is a continuation-in-part of application Ser. No. 09/927,109, filed on Aug. 10, 2001, having a publication No. of 2003/0032940, now U.S. Pat. No. 6,745,998 A1.

BACKGROUND

This invention relates to an improved male luer connector device that attaches to a female luer valve to open a flow channel through the male luer. Once the engagement of the luers has been established, these valves are used to make connections in hospitals for intravenous (IV) devices in order to be used in medical liquid flow applications.

Luer devices are used in particular in a variety of medical applications where there is a desire to interconnect together male and female connector parts onto tubing material that is connected to an IV. The most common types of IV fluid exchanges use a syringe fitted with a nozzle that is designed to be received into a corresponding receiver attached to the IV device. The receiver often has a hollow tubular cannula or post that routes fluid into a line inserted into the IV extending into the patient's veins.

Typical luer connections utilize a male luer connector that is inserted into a female luer connector. The male luer connector is threaded onto corresponding threads of the female luer connector to engage the two so that fluid may be passed between them without escaping or leaking from the connection. Because these connections are subject to coming loose or disengaging, there is always a possibility that fluid being passed within these tubes can escape. When using hazardous drugs, such as those used for chemotherapy treatments, the possibility of escaping fluids can be a dangerous problem. Additionally, even if the fluid does not leak when the connectors are engaged, once they are disengaged, the residual amount of fluid remaining on the tip of the connectors can still be harmful. While this amount may be less than an amount Therefore, there is a need for a luer connection that securely contains the fluid materials included therein when luers are engaged to one another. There is also a need for a luer connection that seals off the male luer connector in a male-female connection so that users of the connector are protected from hazardous drugs that remain on the luer tip surface when disengaged.

SUMMARY OF THE INVENTION

Briefly, and in general terms, the invention is directed to a male valved connector that creates a partial vacuum upon disengagement from a female connector to draw fluid disposed at an interface between the male and female connectors away from the interface.

In accordance with aspects of the present invention, there is provided a male Luer connector for connection with a female Luer connector for medical fluid flow, the female connector having a front contact surface and an internal valve, the male Luer connector comprising a tubular housing having a distal end and a proximal end, the distal end configured to engage the female Luer connector and establish an interface and vacuum means for creating a partial vacuum at the distal end of the tubular housing during disengagement of the male connector from the female connector during a time period when the female valve is closed, whereby the vacuum means draws fluid residing at the interface away from the interface during disengagement of the male and female connectors. In more detailed aspects, the vacuum means is located within the tubular housing, and comprises a first valve controlling the flow of fluid through the proximal end of the tubular housing. The vacuum means also comprises a second valve controlling the flow of fluid through the distal end of the tubular housing and the vacuum means is also for controlling the second valve to remain open while the vacuum means creates the partial vacuum.

In further detailed aspects in accordance with the invention, the vacuum means is also for controlling the first valve to close first, and controlling the second valve to remain open after the female connector valve closes during disengagement of the female connector from the male connector. The vacuum means comprises an actuator that controls the opening and closing of the first and second valves and further comprises an actuation surface disposed so as to be moveable by the front contact surface of the female connector to control the actuator to open and close the first and second valves. The first valve comprises a proximal valve disposed at the proximal end of the tubular housing, the second valve comprises a distal valve disposed at the distal end of the tubular housing, and the actuator is disposed within the tubular housing to open and close both the proximal and distal valves.

In yet further aspects, the vacuum means further comprises a resilient member disposed to bias the actuator to close both the proximal and distal valves. The resilient member has an inner variable-volume cavity through which fluid flows, the cavity having a first volume when the male connector is disengaged from the female connector, the cavity having a second volume smaller than the first volume when the male connector is engaged with the female connector, whereby the resilient member creates a partial vacuum when moving from the second volume to the first volume during closure of the distal valve occurring when the female and male connectors are being disengaged. In more detail, the cavity has the second volume when the male and female connectors are engaged and the cavity moves to the first volume thereby creating the partial vacuum when the male and female connectors are being disengaged.

In even further detailed aspects, the resilient member forms a valve seat for the distal valve and a valve seat for the proximal valve and the actuator provides a distal valve member for the distal valve that fits into the distal valve seat to close the distal valve and provides a proximal valve member for the proximal valve that fits into the proximal valve seat to close the proximal valve. The resilient member provides the actuation surface, the actuator is disposed within the resilient member in contact with the resilient member, and movement of the resilient member due to engagement with the front contact surface of the female connector causes corresponding movement of the actuator to open and close the distal and proximal valves.

In other aspects, there is provided a male connector for connection with a female connector to establish a path for medical fluid flow, the female connector having a front contact surface and an internal valve, the male connector comprising a tubular housing having a distal end and a proximal end, the distal end configured to engage the female Luer connector and establish an interface, a first valve seat disposed for use in controlling the flow of fluid through the distal end of the tubular housing, an internal plug disposed within the tubular housing, the internal plug having a first valve member that engages the first valve seat to prevent the flow of fluid past the first valve seat, and a resilient member disposed within the tubular housing so as to bias the internal plug to engage the first valve seat, the resilient member having an inner variable-volume cavity through which fluid flows, the cavity having a first volume when the first valve is closed, the cavity having a second volume smaller than the first volume when the first valve is open, wherein the resilient member is disposed so that engagement of the female connector with the male connector causes the resilient member cavity to move to the second volume and disengagement of the female connector from the male connector causes the cavity to move from the second volume to the first volume thereby creating a partial vacuum.

In accordance with aspects of a method in accordance with the invention, there is provided a method for disengaging a male connector from a female connector, the male connector including a distal end engaged with the female connector, a proximal end, and an internal valve and the female connector including a proximal end engaged with the male connector, a distal end, and an internal valve, the method comprising closing a first valve in the male connector at the proximal end of the male connector to isolate an interface between the male connector and the female connector from fluid at the proximal end of the male connector, and creating a partial vacuum at the interface of the male connector and female connector to draw fluid at the interface away from the interface. In further more detailed aspects, the method further comprises the step of closing the internal valve of the female connector during the step of creating a partial vacuum. The method also further comprises the step of closing a valve at the distal end of the male connector after the step of creating a partial vacuum. The method wherein the step of creating a partial vacuum comprises creating a partial vacuum within the male connector and drawing fluid at the interface into the male connector.

These and other features and advantages of the present invention will become apparent from the following detailed description of preferred embodiments which, taken in conjunction with the accompanying drawings, illustrate by way of example the principles of the invention.

BRIEF DESCRIPTION OF THE DRAWINGS

The present invention will be better understood from the following detailed description of an exemplary embodiment of the invention, taken in conjunction with the accompanying drawings in which like reference numerals refer to like parts and in which:

FIG. 1 is a side view of the two components of the male to female luer connection of the luer fitting;

FIG. 2 is an enlarged sectional view taken on line 2—2 of FIG. 1;

DETAILED DESCRIPTION OF THE DRAWINGS

Figure 3:
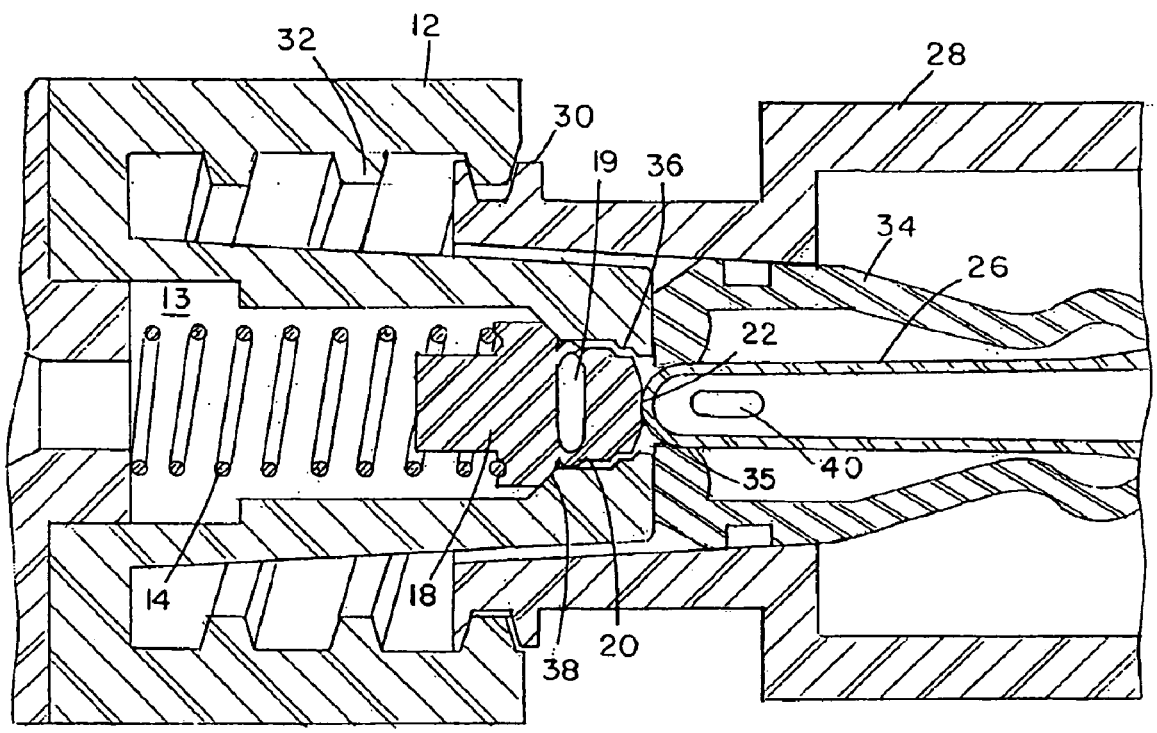
FIG. 3 is a view similar to FIG. 2, with the components partially engaged.

FIG. 1 is a side view of the two components of the male to female luer connection of the luer fitting. The fitting is comprised of a male luer 10 that is intended to engage with a female luer that has an existing flush top female luer valve. The female luer 24 is not limited to a particular type but an exemplar luer is illustrated here. The female luer illustrated here is one where the valve shuts off. This female luer 24 contains a housing element 28 with a cannula or post 26. On the outer surface of the forward end of the housing 28 there are threads 30 that permit engagement of the female luer 24 with the male luer 10. In this embodiment the male luer 10 is comprised of a housing element 12. The inner wall of the housing 12 contains threads 32 that engage the complimentary threads 30 of the female luer connector. Housing 12 has an inner tubular portion 16 of reduced diameter that projects forwardly that has a first necked area 36 and a second necked area 38 (See FIG. 2). The inner tubular portion defines an internal chamber 13 with a forward opening 33 (See FIG. 2). A valve member 18 is biased into an extended position sealing opening 33 by resilient member or spring 14. Spring 14 acts between distal end of chamber 13 and valve member 18. (As used herein, "distal" is the rearward end of the male luer and "proximal" is the forward end, i.e., the left and right ends in the views as illustrated in FIGS. 1 and 2). Valve member 18 includes a resilient portion 20 and a forward tip member 22. FIG. 1 illustrates the two luers 10, 24 in the unengaged position. Other types of female luer valves that do not contain a cannula or post. By way of example, U.S. Pat. No. 5,676,346 by Leinsing and U.S. Pat. No. 5,782,816 by Werschmidt illustrate these types of luer valves.

FIGS. 2 to 5 illustrate the male luer 10 and the female luer 24 as they become engaged with one another. FIG. 2 illustrates the two luers 10, 24 when they are completely unengaged. The cannula or post 26 may have an opening 40 for entrance and exit of fluid between the two luers. Other duct systems (not shown) are possible and may be used. The cannula or post 26 is mounted in a chamber within a sleeve 34. This sleeve 34 can be made of rubber or any other suitable resilient material and serves as a valve member stopper. Sleeve 34 has a forward end opening 35 which is sealed shut in the unengaged position of FIG. 2. The male luer has a forward end that has a first necked area 36 and a second necked area 38 spaced rearwardly from the first necked area 36. FIG. 3 illustrates the male luer 10 beginning to be inserted into the female luer 24. Once the threads 30, 32 begin to engage, the forward end 33 of housing 12 pushes the sleeve 34 back until the opening 35 is forced to open over the end of the cannula 26. The cannula or post 26 then comes into contact with the tip of valve member 18 and begins to push it rearwardly so that the cannula or post 26 displaces the valve element front section 22. This movement begins to separate the seal surface of the first necked area 36 from its seat. As the tip member 22 begins to be pushed back, the second resilient portion 20 is collapsed, compressing the valve element cavity 19. This unseals the first necked area 36 and displaces the liquid contained within the cavity 19. This displaced liquid flows temporarily into the female luer valve 24. As this pressure is applied, the valve member is compressed and pushed further inwardly into chamber 13.

Figure 4:
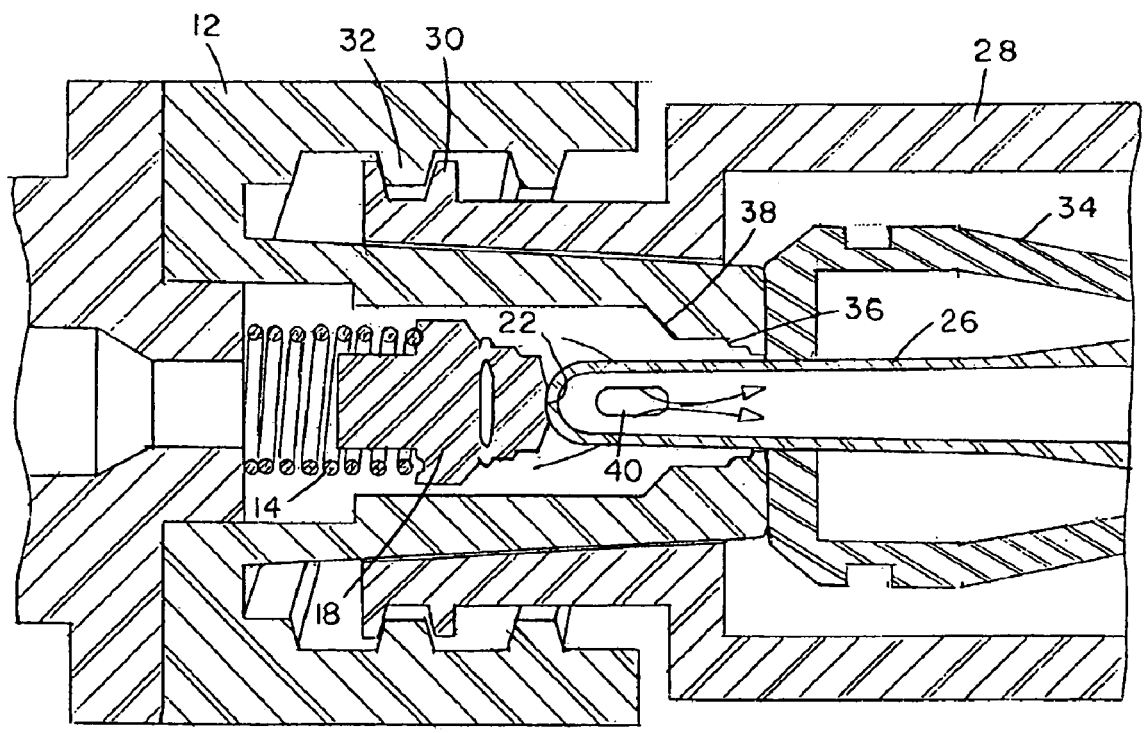
FIG. 4 is a view similar to FIG. 3, with the components fully engaged.

FIG. 4 illustrates the positioning of the luer members when the female 24 and male 10 luers have been even further engaged. The cannula or post 26 begins to push even more onto the tip member 22 and collapse the first resilient member 14 so that the second necked area 38 is unsealed. At this point, more liquid is displaced by the further insertion of the cannula or post into the vacuum section 21 of the male luer as indicated by the arrows in FIG. 4. The opening 40 on the cannula or post 26 permits fluid to pass into and out of the female luer 24. This displaced liquid creates the volume which will be refilled when the action is reversed.

Upon disconnection of the male luer 10 valve from the female luer valve 24, the volume of liquid that was displaced during the connection of the two valves is restored to the original positions, thus creating a relative vacuum. When the female luer 24 is removed from the male luer 10, the main seal created by the second necked area 38 makes contact with its seat. This isolates the vacuum section 21 from the upstream liquid. As the cannula or post 26 is withdrawn, cavity 19 is restored as resilient portion 20 resiles to its uncollapsed natural shape. As this restoration occurs, liquid is drawn into cavity 19. Because the second necked area 38 is closed, this liquid will be drawn from the interface between the male luer 10 and the female luer 24. This effect is enhanced by the volume represented by the cannula or post 26, which must be replaced as the cannula or post 26 is withdrawn. The relative vacuum created will attempt to draw liquid into the vacuum section until the seal surface of the first necked area 36 again contacts its seat.

Figure 5:
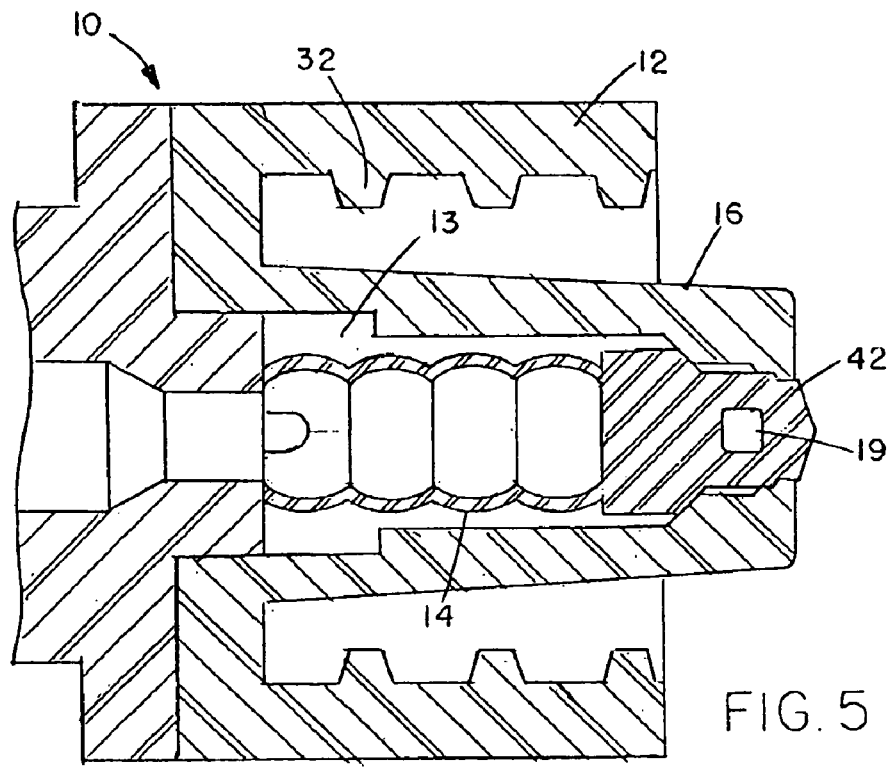
FIG. 5 is a view similar to a portion of FIG. 2, showing an alternative integrated spring member.

FIG. 5 illustrates the same type of dual stage valve as above only that it is formed with the spring 14 integrally connected to the valve member 42. The housing 12 contains the inner sleeve 16 and positioned inside of the inner sleeve 16 is an inner chamber 13. The function of this embodiment is the same as the previously described embodiments with the exception that the spring 14 can be comprised of elastomeric or other types of material that are integrally connected with the valve member 42.

Figure 6:
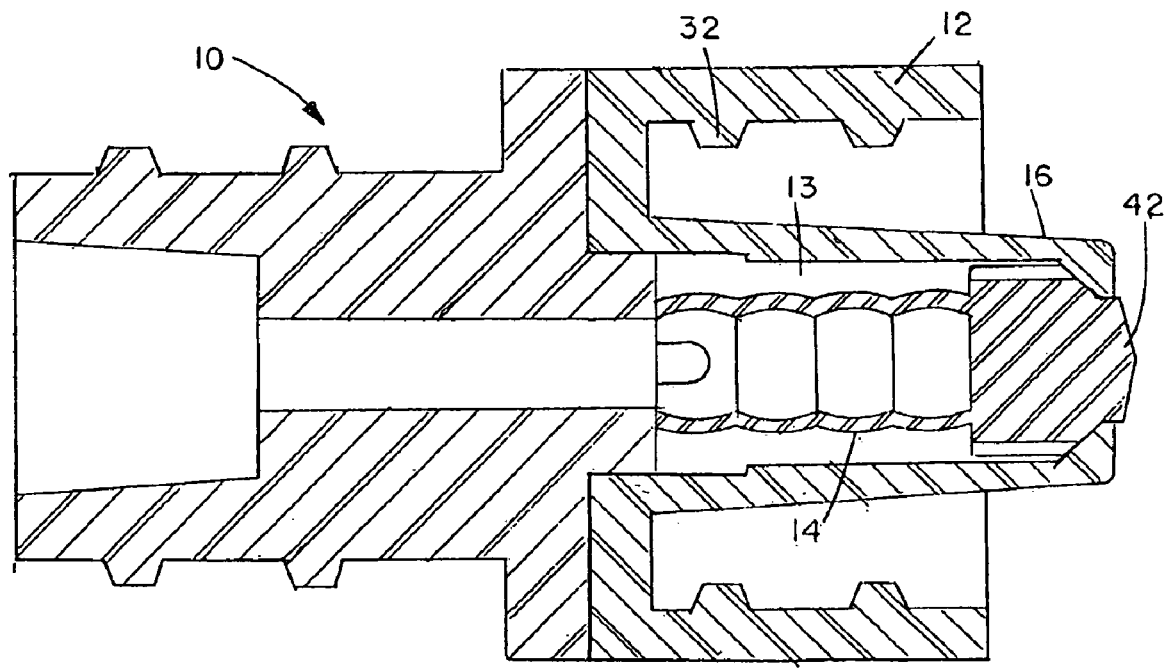
FIG. 6 is a view similar to FIG. 5, showing an alternative single stage valve.
Figure 7:
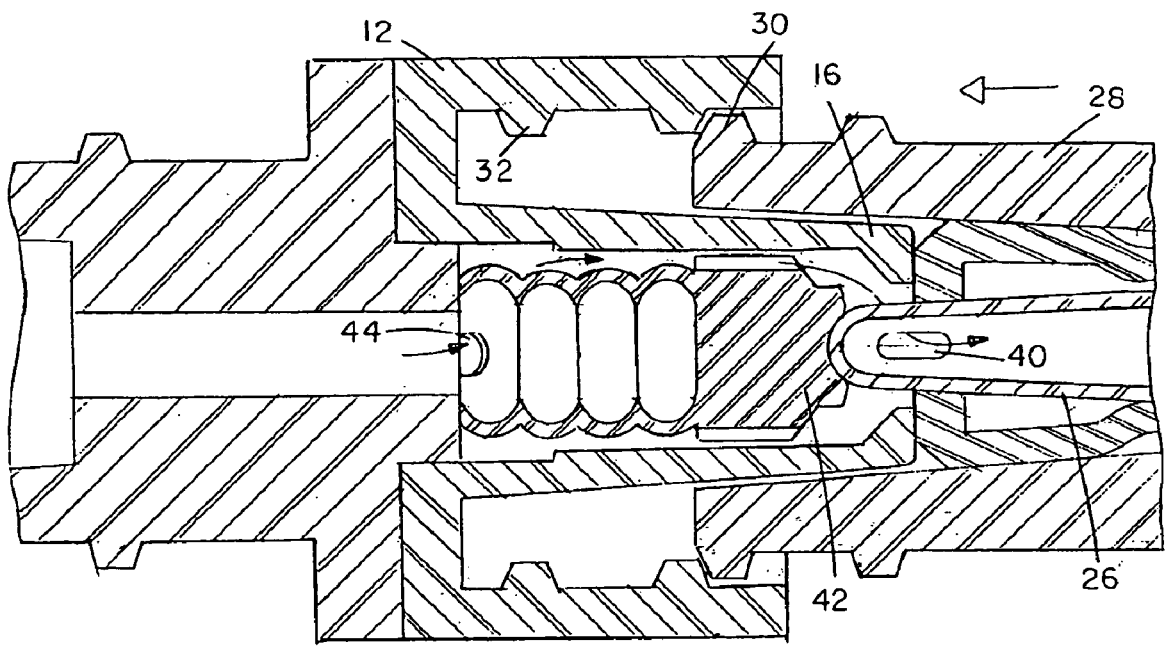
FIG. 7 is a view similar to FIG. 6, showing the valve opened.

FIGS. 6 and 7 illustrate a male luer according to another embodiment of the present invention. This apparatus is a single stage luer valve with an integral resilient member. In this embodiment, the male luer has a housing 12 with threads 32 on the inner wall of the housing for engagement to the complimentary threads on the female luer 30. The inner chamber 13 is sealed by a valve member 42 that is integrally formed with the resilient member and the tip. This new valve member 42 therefore functions as in the previous embodiment except that all members are formed in one piece, rather than including a separate resilient member. This embodiment demonstrates a single stage luer valve in that once the female luer engages with the valve member 42, the member 42 moves as a single piece rather than as several different pieces as described above. FIG. 7 illustrates the luer of FIG. 6 engaged with a female luer 24 and permitting fluid flow. Once the two luers 10, 24 are engaged, the cannula or post 26 of the female luer 24 collapses the valve member 42 and permits fluid flow via the opening 40 in the cannula or post 26 and also via an opening 44 in the rear end of the valve member 42.

Figure 8:
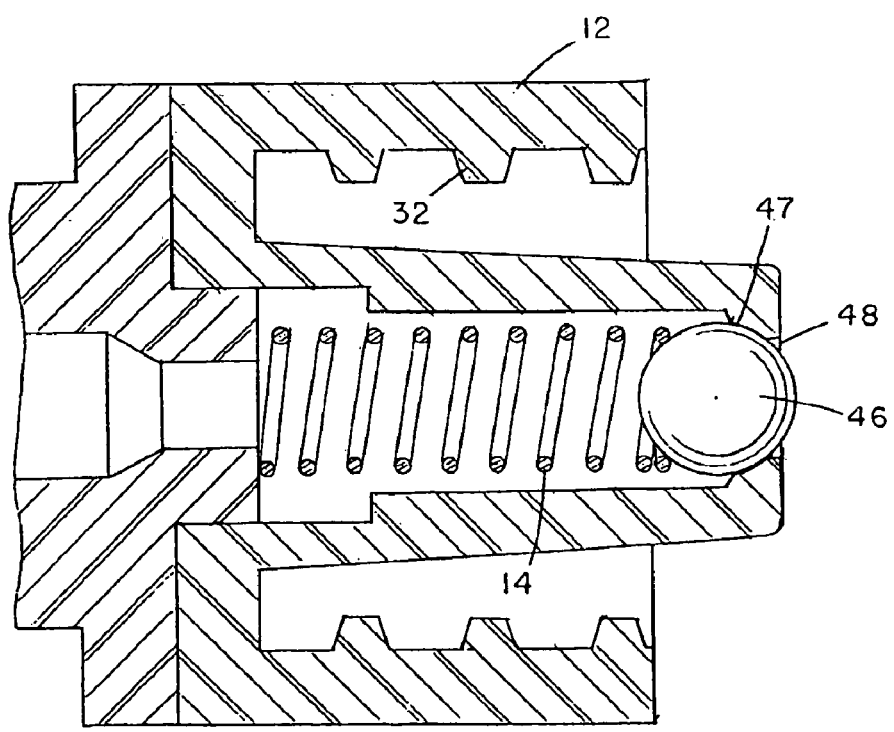
FIG. 8 is a view similar to FIG. 5, showing a ball type valve.

FIG. 8 illustrates another embodiment of the present invention. In this embodiment, the housing 12 of the male luer is similar to the previous embodiments. Additionally, contained within the inner sleeve 16 is a resilient member or spring 14. However, in this embodiment, the valve contained on the end of the resilient member is shown as a ball 46. This ball may be made of various types of materials as for example, elastomeric material. Additionally, the forward end opening of chamber 13 is exemplified as a part-spherical seat 47 to accommodate for ball valve 46. Those skilled in the art will recognize that the valve contained on the end of the resilient member or spring 14 can be of a variety of shapes. However, the shape of the tip of the male luer 10 needs to be one that corresponds to the shape of the tip of the female luer 24.

Figure 9:
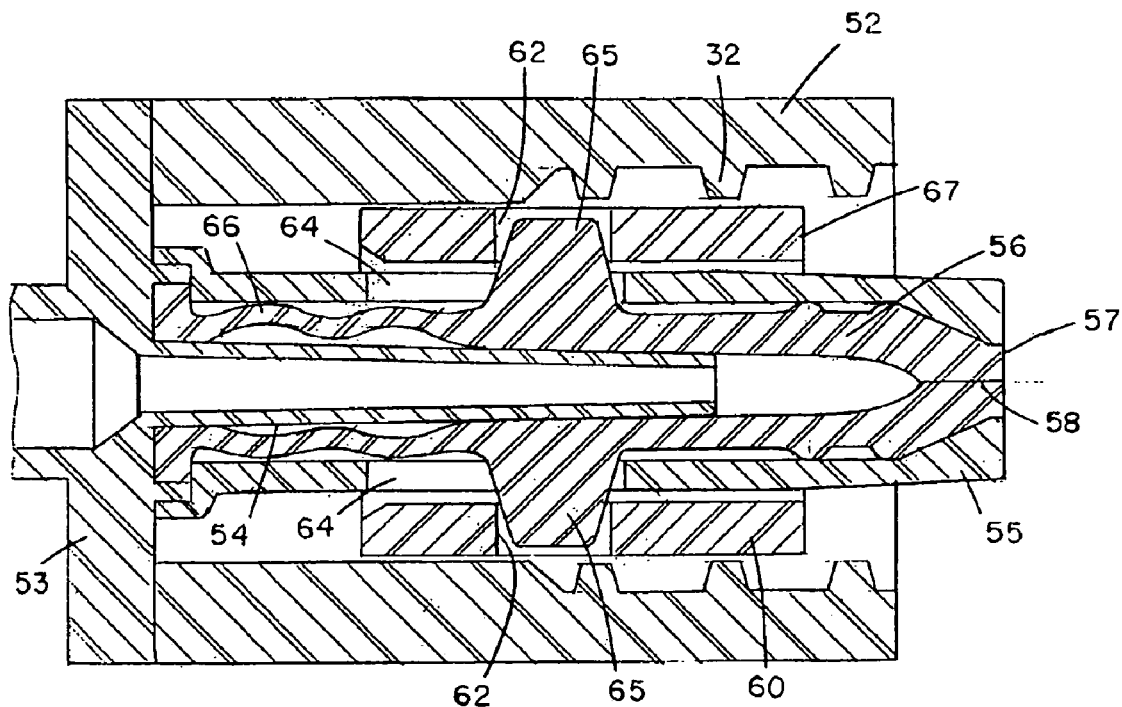
FIG. 9 is a sectional view showing an alternative slide actuated valve.
Figure 10:
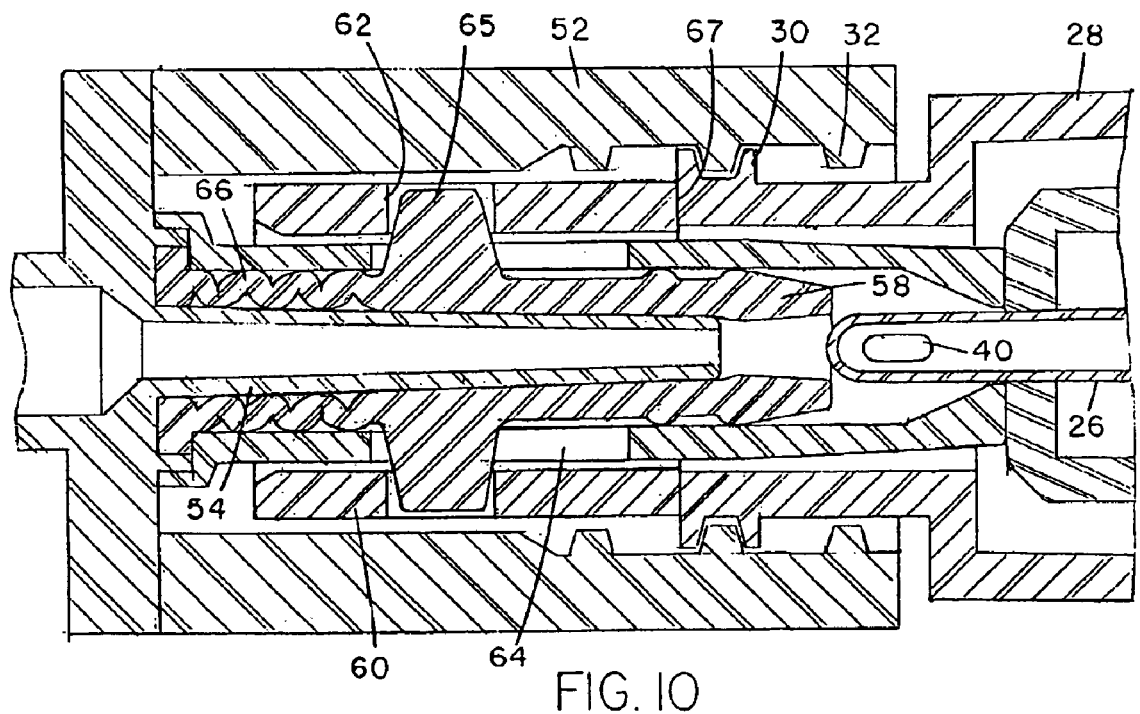
FIG. 10 is a view similar to FIG. 9, showing the valve opened.

FIGS. 9 and 10 illustrate a modified connector according to yet another embodiment of the present invention, in which a modified male luer is releaseably securable to the female luer 24 of the previous embodiments. The modified male luer comprises a housing with a cylindrical outer wall 52 and an inner tubular support 54 which projects into the cylindrical housing from rear end 53 and extends along part of the length of the housing. Outer wall 52 has internal threads 32 for engaging the female luer threads 30 and a larger diameter than the inner support 54 which extends from the rear end 53 of the housing and projects out of the forward end of the housing. A resilient sleeve or bladder member 56 is secured between the tubular member 55 and support 54 at its rear end, and projects forwardly within tubular member 55 to its forward end opening 57. Bladder member 56 has a forward end opening 58 which is sealed shut by the inwardly tapered end portion of the tubular member 55 when in the extended, unconnected position of FIG. 9. The forward end portion 58 of bladder member 56 acts as a valve to seal the end opening 57 of the male luer in the position illustrated in FIG. 9.

Tubular member 55 of the male luer is of smaller diameter than the inner cylindrical wall 52 of the housing, to leave an annular gap between the member 55 and inner wall 52. A sliding sleeve 60 is slidably mounted over the tubular member 55 in this annular gap. Sleeve 60 has diametrically opposed openings 62, and the tubular member 55 has opposing elongate, axially extending slots 64. Oppositely directed guided portions 65 (e.g., tabs, wings or fins) on the inner bladder or sleeve member 56 project radially outwardly through the slots 64 and into the openings 62. Thus, when the sleeve is in the fully extended position of FIG. 9, it will pull the sliding sleeve forwardly into the illustrated position. The corrugated portion 66 of bladder member 56 acts as a spring to bias the forward end of the bladder member 56 and the sliding sleeve 60 into the extended position.

FIG. 10 illustrates a female luer 24 connected to male luer 50. As the forward end of the female luer housing is threaded into the cylindrical wall of the male housing, it will engage the forward end 67 of the sliding sleeve 60, urging the sleeve, and thus the bladder member 56, rearwardly and moving the forward end portion of the bladder member out of sealing engagement with the forward end opening of tubular member 55. This permits the forward end opening 58 to spring open, as indicated. At the same time, the forward end of tubular member 55 will force the sleeve 34 in the female luer rearwardly so that it passes over the end of cannula 26, which then extends into the open forward end of the tubular member. This allows fluid flow through the two luers, via the inner tubular support, open end 58 of the bladder member 56, and the openings 40 in the cannula 26. When the luers are disconnected, the compressed corrugated portion 66 of the bladder member 56 urges the forward end portion to move back into sealing engagement with the forward end of the tubular member 55, preventing any fluid leakage.

Figure 11:
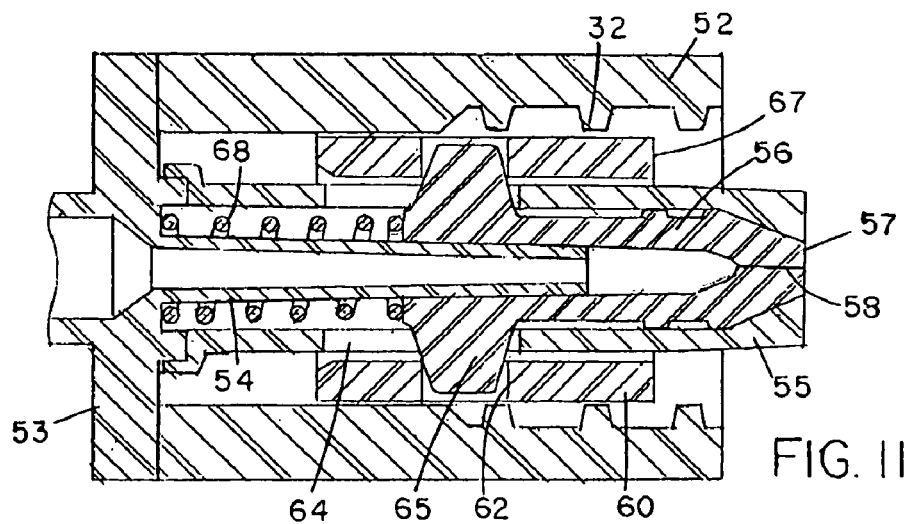
FIG. 11 is a view similar to FIG. 9, showing an alternative slide actuated valve.

FIG. 11 is a view similar to FIG. 9, showing an alternative slide actuated valve except that the resilient sleeve or bladder member 56 does not have a corrugated portion and instead has a separate spring member 68. The spring member 68 can any type as for example, those made of metal or elastomeric material. The function of the male luer valve is the same; it is merely the spring member 68 that replaces the previous corrugated member.

Figure 12:
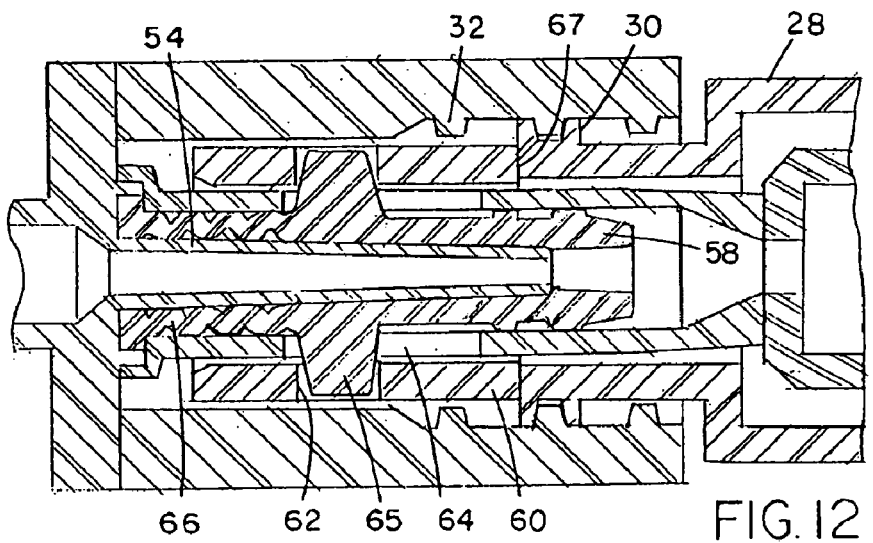
FIG. 12 is a view similar to FIG. 10, showing an alternative valve for use with a female luer valve that does not have a cannula or post.

FIG. 12 is a view similar to FIG. 10, showing an alternative valve for use with a female luer valve that does not have a cannula or post. The outer surface of the forward end of the housing 28 engages and compresses the forward end 67 of the sliding sleeve 60 of the male luer valve. As the forward end of the female luer valve housing 28 continues to further displace the sliding sleeve 60, the bladder member 56, continues to move rearwardly and moves the forward end portion of the bladder member out of sealing engagement with the forward end opening of the tubular member 55. This permits the forward end opening 58 to spring open. This allows fluid flow through the two luers, via the inner tubular support, open end 58 of the bladder member 56. Once the luers are disconnected, the sealing engagement as previously described once again occurs.

Figure 13:
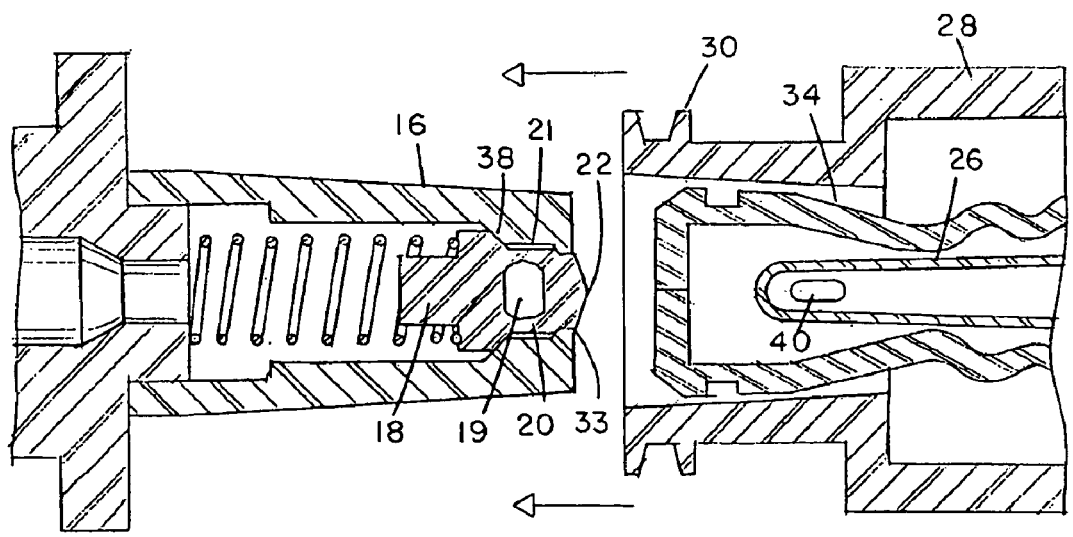
FIG. 13 is an illustration of a male luer valve that does not contain a housing element.

FIG. 13 is an illustration of a male luer valve that does not contain a housing element. This view is similar to FIG. 2 except that the male luer valve is not contained within a housing element and instead can be self-sustained. However, the function of the male luer valve is the same as that explained for FIG. 2 only that the engagement with the female luer housing does not occur with the male luer housing.

Figure 14:
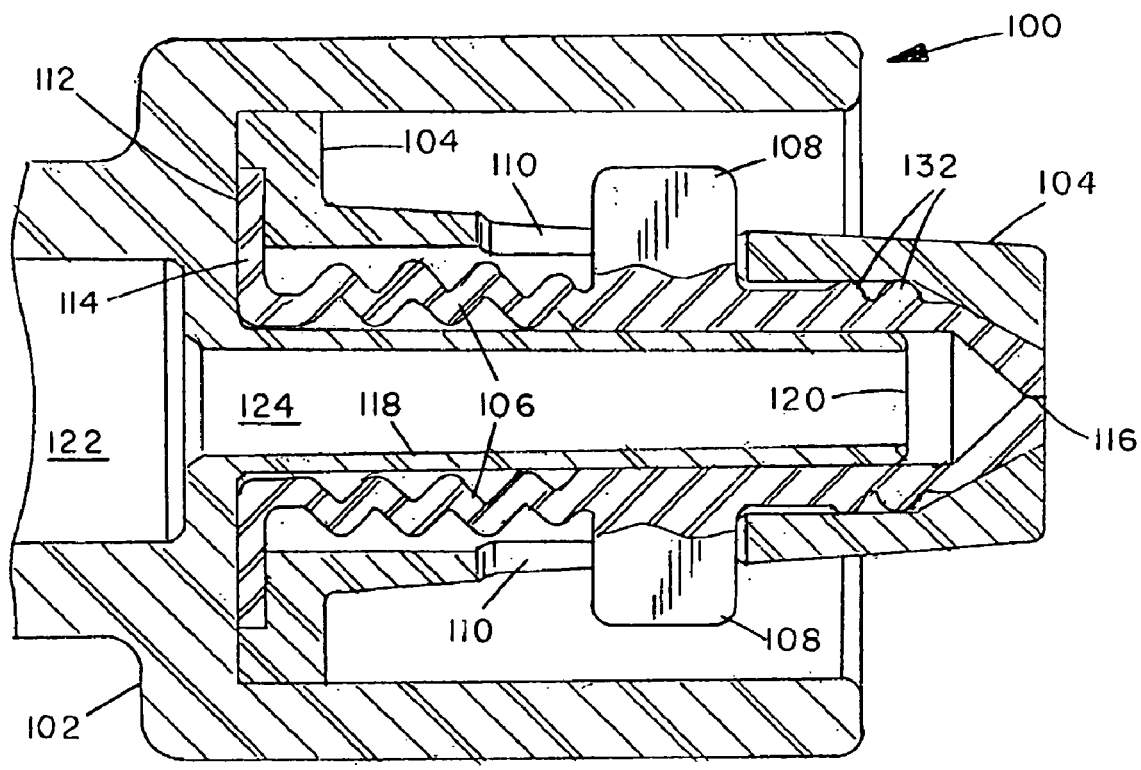
FIGS. 14 and 15 are views similar to FIG. 11 illustrating a male luer which does not contain a sleeve and showing the movement from a closed position (FIG. 14) to an open position (FIG. 15) for the male luer during contact with a female luer having no core rod or cannula.
Figure 15:
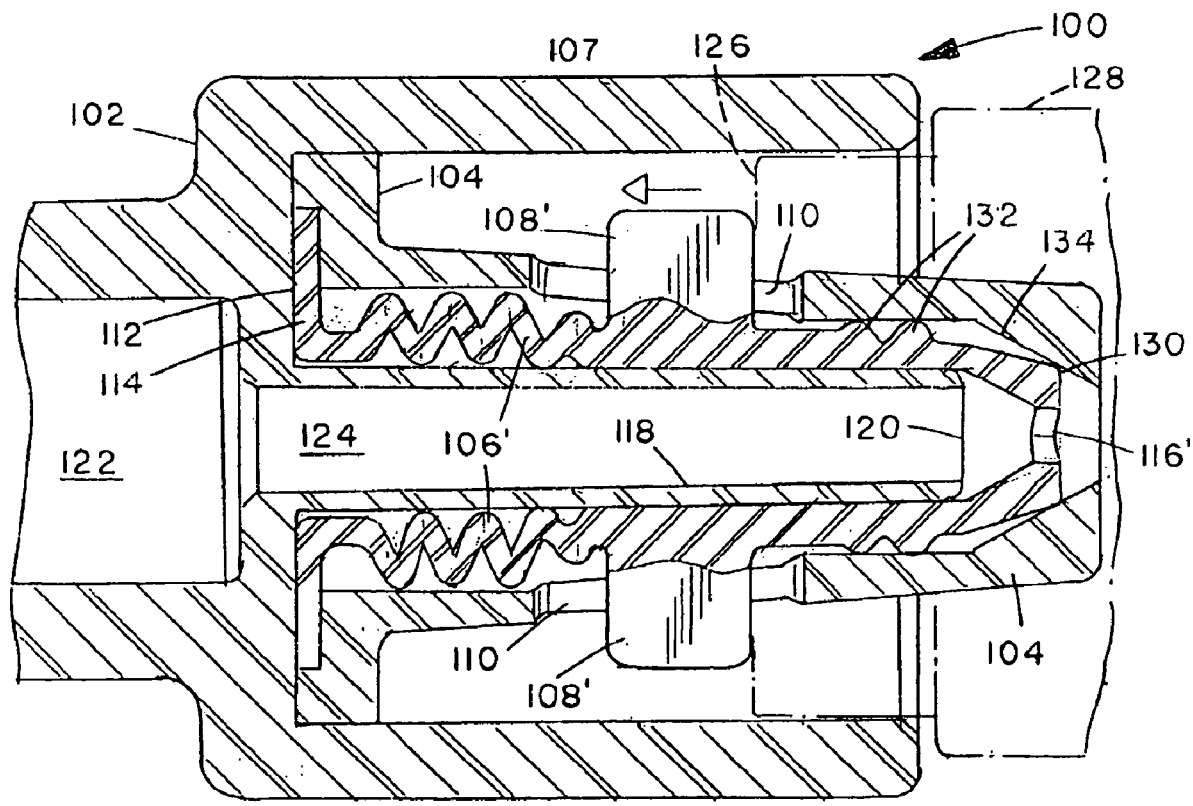

FIGS. 14 and 15 illustrate an embodiment of a male luer 100 which does not contain a sliding sleeve 60. The luer housing 102 has a tubular projecting conduit 118 over which is positioned resilient sleeve or member 106. The base 114 of resilient member 106 is butted against the interior end wall 112 of housing 102 and secured in place by the inner end of tubular projecting member 104. The resilient member 106 has one or more laterally projecting fins 108 which are disposed respectively in slots 110 in the tubular portion of member 104. When the male luer is closed (FIG. 14) the opening at the tip 116 of resilient member 106 is closed, sealing off the open end 120 of the male luer 100. When the male luer is engaged by a female luer 128 which has a contact surface 126 but no central core rod or cannula (FIG. 15) the surface 126 engages the fins 128 and movement of the male luer into the female luer causes the fins to move backward into housing 102 as indicated by arrow 107 with the fins 108 guided within the slots 110 as shown at 108' to compress the bellows portion of the resilient member as shown at 106'. This opens the tip as shown at 116' to allow fluid flow through opening 120 into the flow channels 124 and 122 of conduit 118 and housing 102 respectively. The peripheral projections 132 function as O-ring seals and when the luers are engaged the projecting front edge 130 of the resilient member 106 engages the inner sloped surface 134 of member 104 to provide a sealing or "stopper" effect and keep the O-ring seal area free of the fluid flow and dry.

For simplicity in a number of the Figures the female luer 128 is not itself shown and only the movement of elements of the male luer 100 is illustrated. It will be understood that such movement is the result of the male/female luer engagement in the manner illustrated in other Figures such as (but not limited to) FIGS. 2, 3, 12 and 15. Similarly, threads or other securing devices to retain the male and female luers in their engaged positions during flow of fluid through them are also for simplicity not shown in all Figures, but it will understood that such are present as illustrated in (but not limited to) FIGS. 2, 3, 4, 10 and 12.

Figure 16:
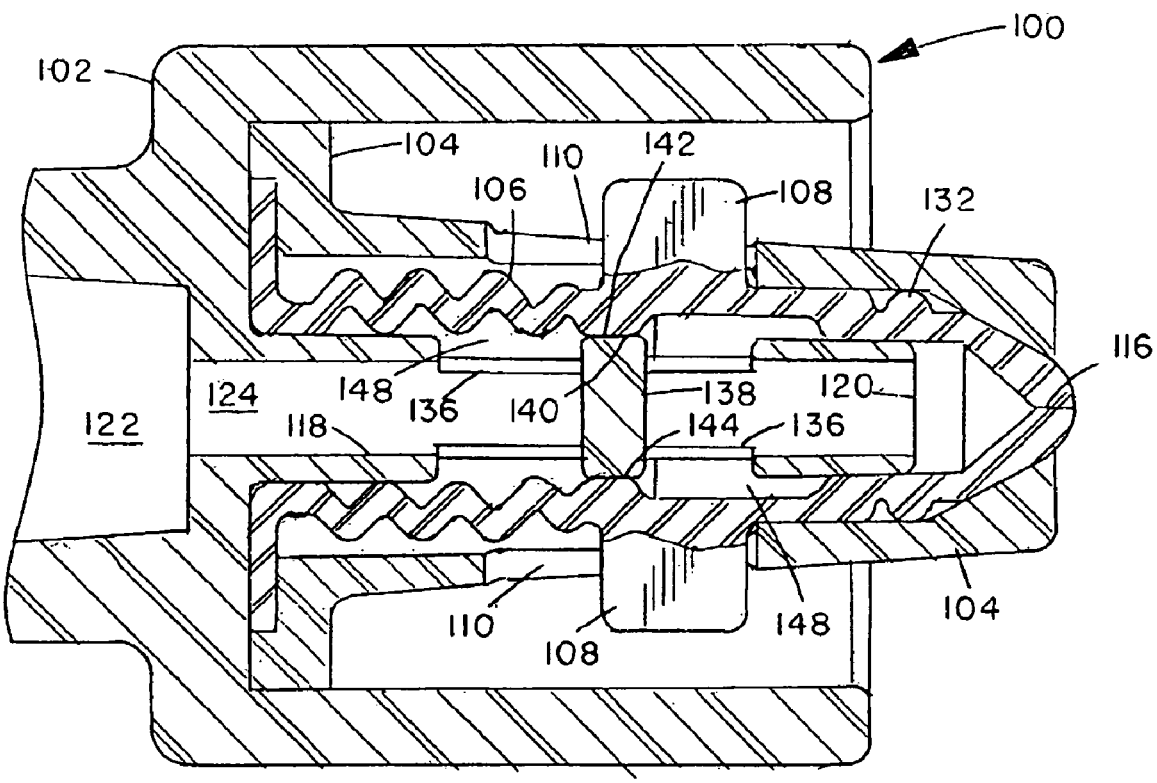
FIGS. 16 and 17 are views similar to FIGS. 14 and 15 illustrating a male luer having a central sealing member internally of the resilient member and showing the movement from a closed position (FIG. 16) to an open position (FIG. 17) for the male luer during contact with a female luer having no core rod or cannula.
Figure 17:
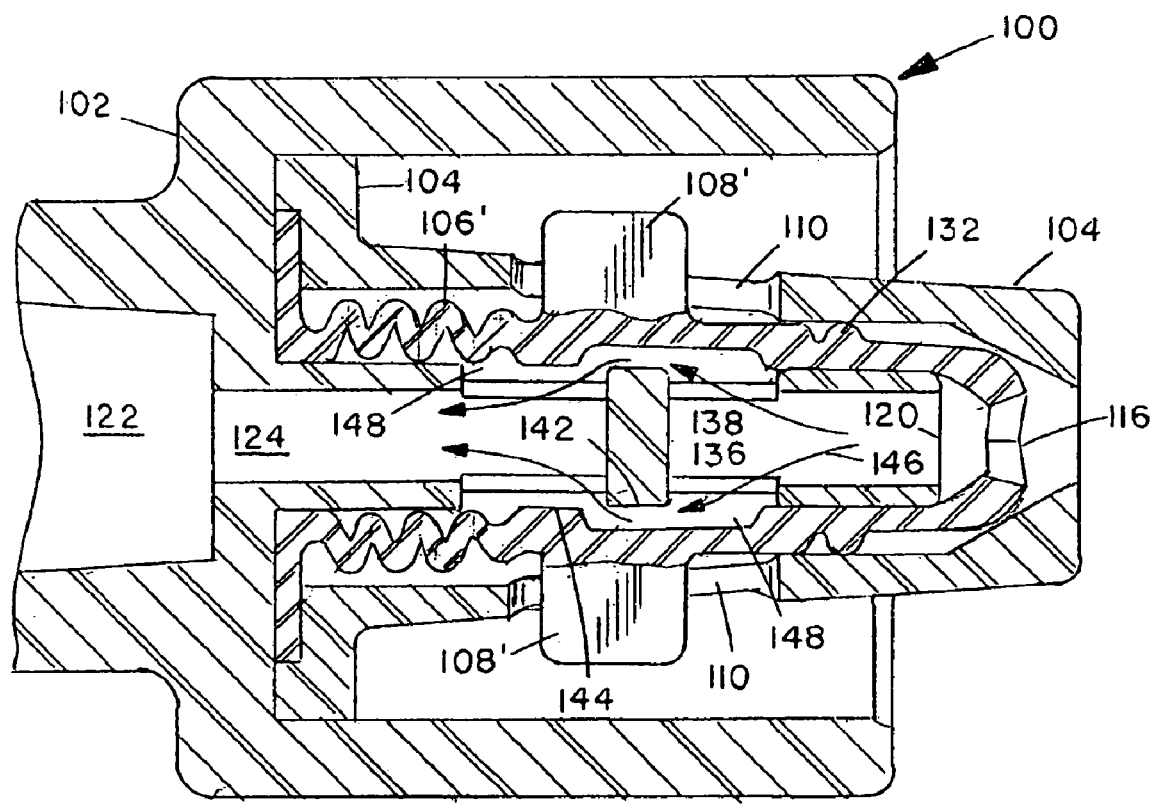

FIGS. 16 and 17 illustrate an embodiment similar to that of FIGS. 14 and 15, but in which there is an internal plug 138 within the conduit 118 with channels 148 past the plug 138. These channels can be formed in the wall of conduit 118 or can be formed by having plug 138 mounted on spaced apart supports (not shown) connected to conduit 118, or in any other convenient manner. The peripheral surface 142 of plug 138 contacts radial land 144 on the inner surface of resilient member 106 as shown at 140 when the male luer is closed (FIG. 16). When the male luer enters the female luer the contact surface 126 contacts the fins 108 and pushes them backward as shown at 108' in FIG. 17, thus compressing the resilient member as shown at 106' and displacing the land 144 from contact with the surface 142 of the fixed plug 138. Compression of the resilient member also opens tip 116 of the resilient member as shown at 116'. Fluid flow through opening 120 into conduit 124 and around plug 138 through channels 148 as shown by arrows 146 is also permitted. The axial position and width of land 114 can be varied to determine when contact with the plug edge 142 is made or lost, thus determining when the luer opens or closes, and also to provide a vacuum effect to prevent or minimize backflow of fluid.

Figure 18:
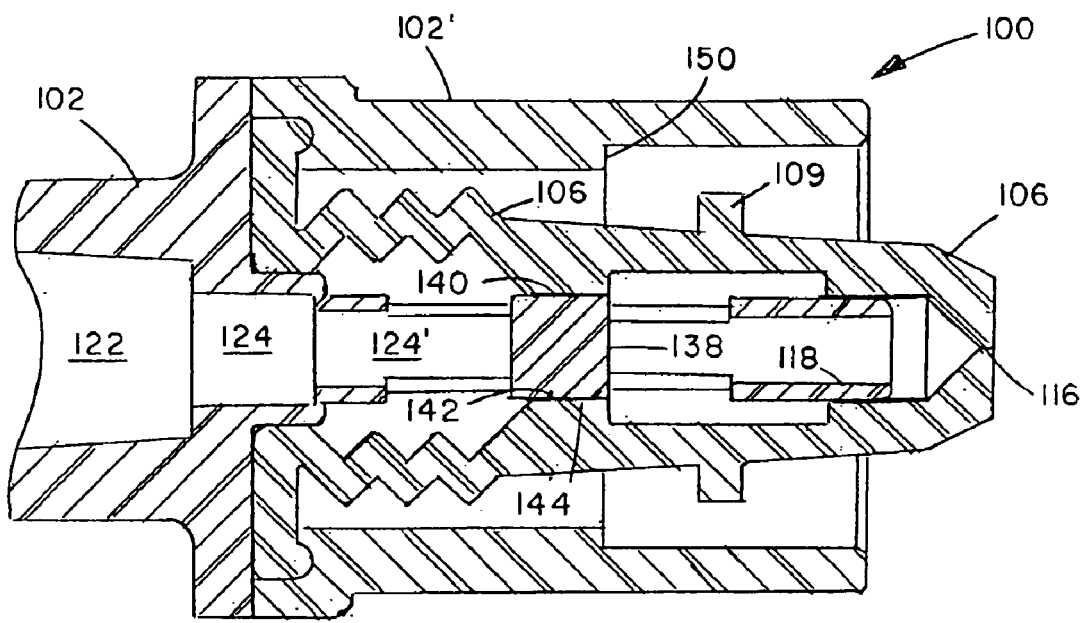
FIG. 18 is a view similar to FIG. 11 illustrating a male luer which has a peripheral flange incorporated into the resilient member which upon contact with the contract surface of a female luer (which has no core rod or cannula) is urged backwards causing the resilient member to retract and open.
Figure 19:
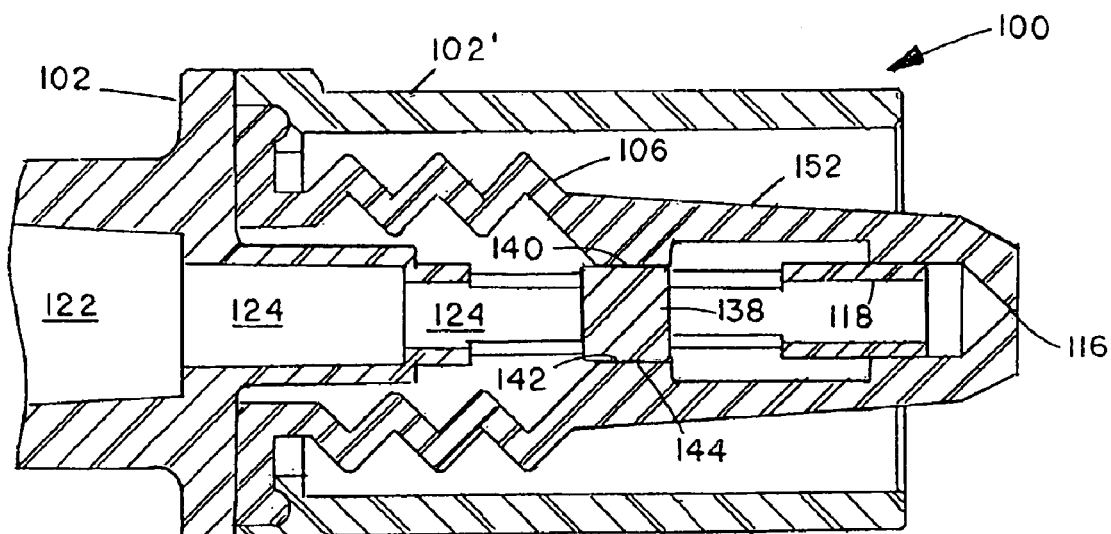
FIGS. 19, 20 and 21 illustrate appearance and operation of male luers which have resilient members with smooth outer contact surfaces which upon contact with the contract surface of a female luer (which has no core rod or cannula) provide a sufficiently frictional connection such that the resilient member is urged backwards causing it to retract and open.
Figure 20:
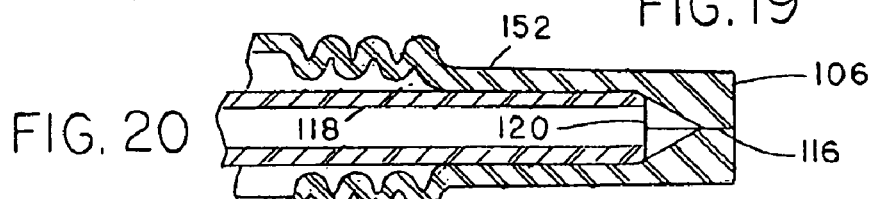
Figure 21:
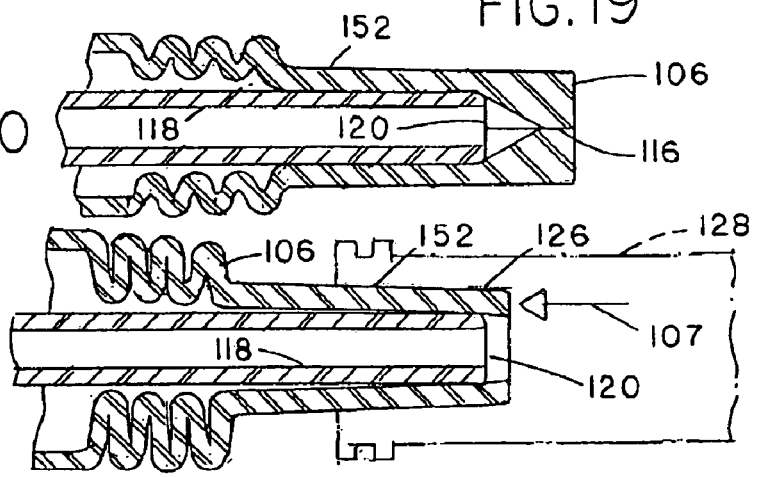

FIGS. 18–21 illustrate embodiments of a "soft" male luer 100 in which the engagement with the female luer 128 results in the contact area 126 of the female luer being the interior surface of the luer which is in contact directly with the exterior surface 152 of the resilient member 106, as illustrated in FIG. 21. In FIG. 18 two optional elements are shown: shoulder 150 and projections 109 which can be fins such as 108, a peripheral flange, protruding structure which can engage the contact surface of the female luer. The shoulder 150 can be a continuous radial shoulder within the portion 102' of the housing 102 or it can consist of spaced-apart projections aligned radially within portion 102'. (Portion 102' is shown in FIGS. 18 and 19 as a member separate but attached to the rest of housing 102, but it can also be integral with the rest of housing 102). Shoulder 150 serves as a limiting device to engage contact surface 126 of the female luer 128 and stop the relative movement of the two luers, thus limiting the depth to which the male and female luers can be engaged. Projections 109 can assist the compressions of the resilient member 106 by sharing engagement with the contact surface 126 with the surface 152 of the member 106. The tip area 116 of the member 106 can be thickened as shown in FIGS. 18 and 19 to provide some expansion into the engaging neck of the female luer and thus create an additional sealing effect.

In FIGS. 20 and 21 the soft male luer 100 is illustrated as having an optional extended housing 102, such that engagement of the surface 152 of member 106 in contact with surface 126 provides the entire engagement of the male and female luers. That engagement and the compression of member 106 over the rigid conduit 118 allow opening of tip 116 and flow through end 120.

Figure 22:
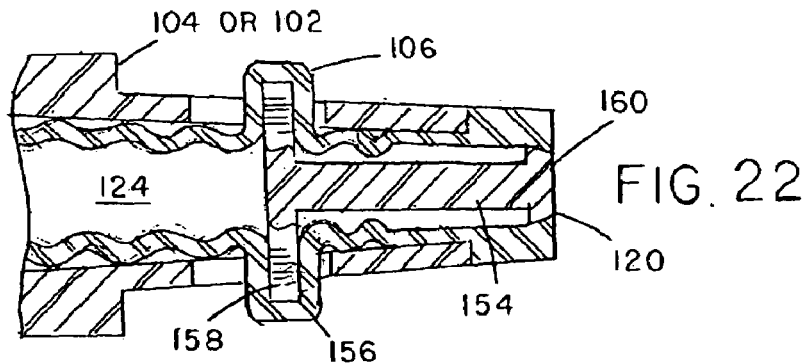
FIGS. 22 and 23 are views similar to FIGS. 16 and 17 illustrating a male luer having a central sealing member internally of the resilient member which has a radially extending portion which protrudes into the wall of the resilient member and extends it outward, allowing it to extend into or through a guide in the housing of the male luer, which guide is engaged by a contact surface of a female luer having no core rod or cannula, such engagement causing the resilient member to retract and open to permit fluid flow between and through the luers.
Figure 23:
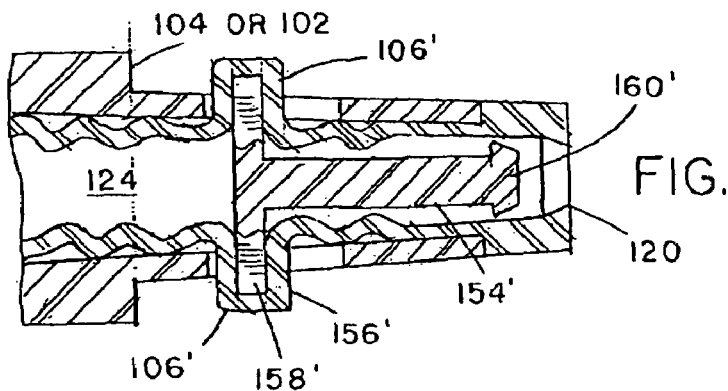
Figure 24:
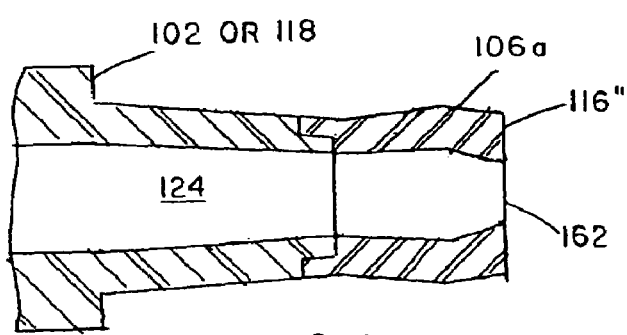
FIGS. 24, 25, 26 and 27 are side elevation views (FIGS. 24 and 26) and end elevation view (FIGS. 25 and 27) of another embodiment of a resilient member of a male luer which has a slightly bulbous tip with a slit opening, which slit is compressed and opened during contact with the interior surface of a female luer with a generally conical contact recess.
Figure 25:
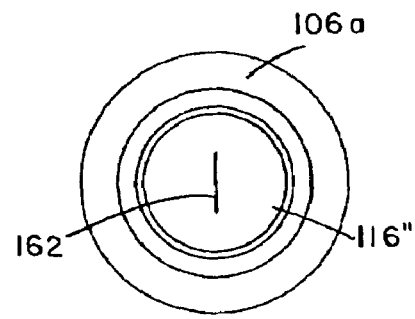
Figure 26:
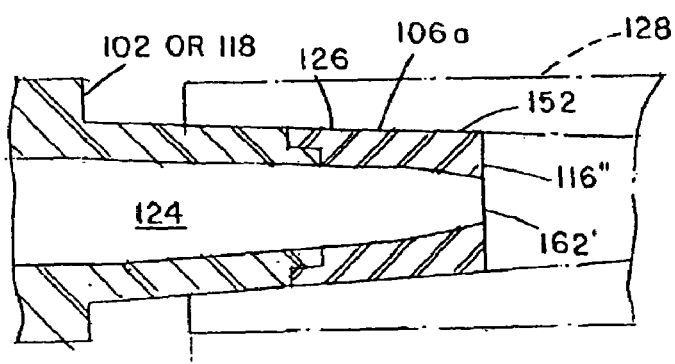
Figure 27:
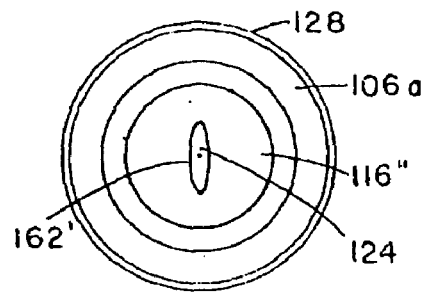

Additional embodiments are shown in FIGS. 22–27. In the embodiment of FIGS. 22 and 23, an internal plug 154 similar in function to that of valve member 42 is shown. The plug 154 has a integral fins or radial flange 158 which is inserted into a radial pocket 156 in resilient member 106. Engagement with the female luer causes the female luer's contact surface to push the resilient member 106, its pocket 156 and fins or flange 158 backward as shown as 106', 156' and 158' respectively, thus withdrawing plug head 160 of plug 154 to the position shown at 160' thus opening end 120 for flow into conduit 124.

FIGS. 24–27 show a shaped resilient member 106a which has a slit 162 in its tip 116". When contacted by the female luer 128, frictional engagement of the outer surface 152 of the resilient member 106a with the contact surface 126 of the female luer causes the resilient member 106a to deform as shown in the Figures, thus opening slit 162 as shown at 162' to allow fluid flow into conduit 124.

Referring now to FIGS. 28 through 32, a male connector 200 in accordance with aspects of the invention and a female connector 202 are shown in various configurations of engagement to demonstrate the sequential valve timing in accordance with aspects of the invention.

Figure 28:
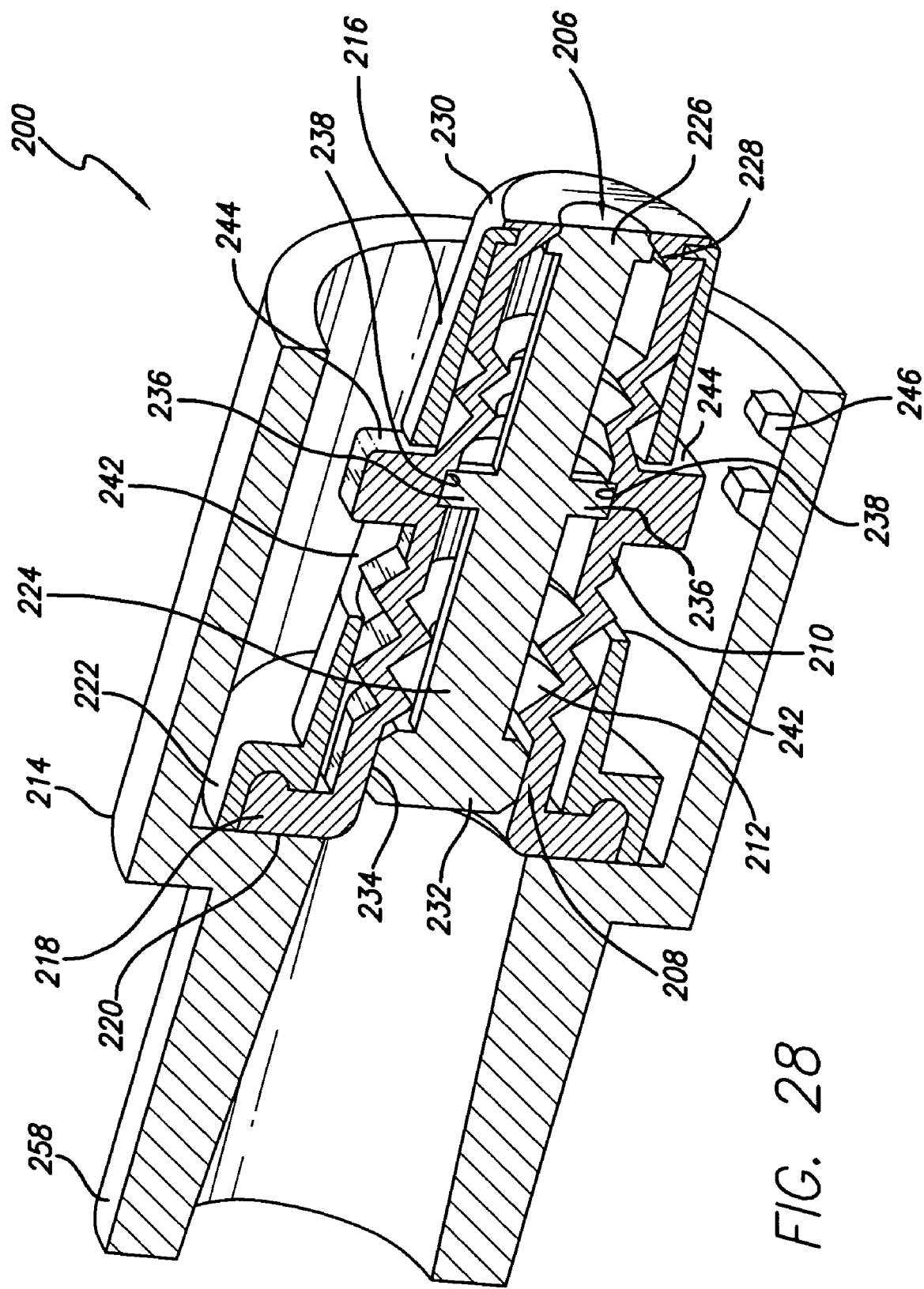
FIG. 28 is a cutaway perspective view of multi-valved male Luer connector in accordance with aspects of the invention for use in obtaining sequential valve timing and generating a partial vacuum at the male Luer connector end to remove excess fluid from the tip during separation from a female connector.

Referring now to FIG. 28, the male connector 200 is shown in a cutaway perspective form and includes a resilient member 210 having an internal cavity 212. The resilient member is uncollapsed and the internal cavity has a first internal volume. The resilient member is mounted within a housing 214 and within a tubular projecting member 216. The base 218 of the resilient member is butted against the interior wall 220 of the housing and secured in place by the proximal end 222 of the tubular projecting member. An internal plug 224 is mounted within the resilient member. The plug includes a distal valve member 226 that mates with a valve seat 228 provided by the distal end 230 of the resilient member. The internal plug includes a proximal valve member 232 that mates with a proximal valve seat 234 provided by the resilient member, which in this embodiment, results in a type of poppet valve 208. The internal plug includes integral fins or radial flanges 236 that are inserted into radial pockets 238 formed in the resilient member. The resilient member provides a biasing force in the distal direction and tends to return itself and the internal plug to the configuration shown in FIG. 28 unless opposing forces in the proximal direction cause partial collapse or compression of the resilient member, as is discussed below.

Figure 29:
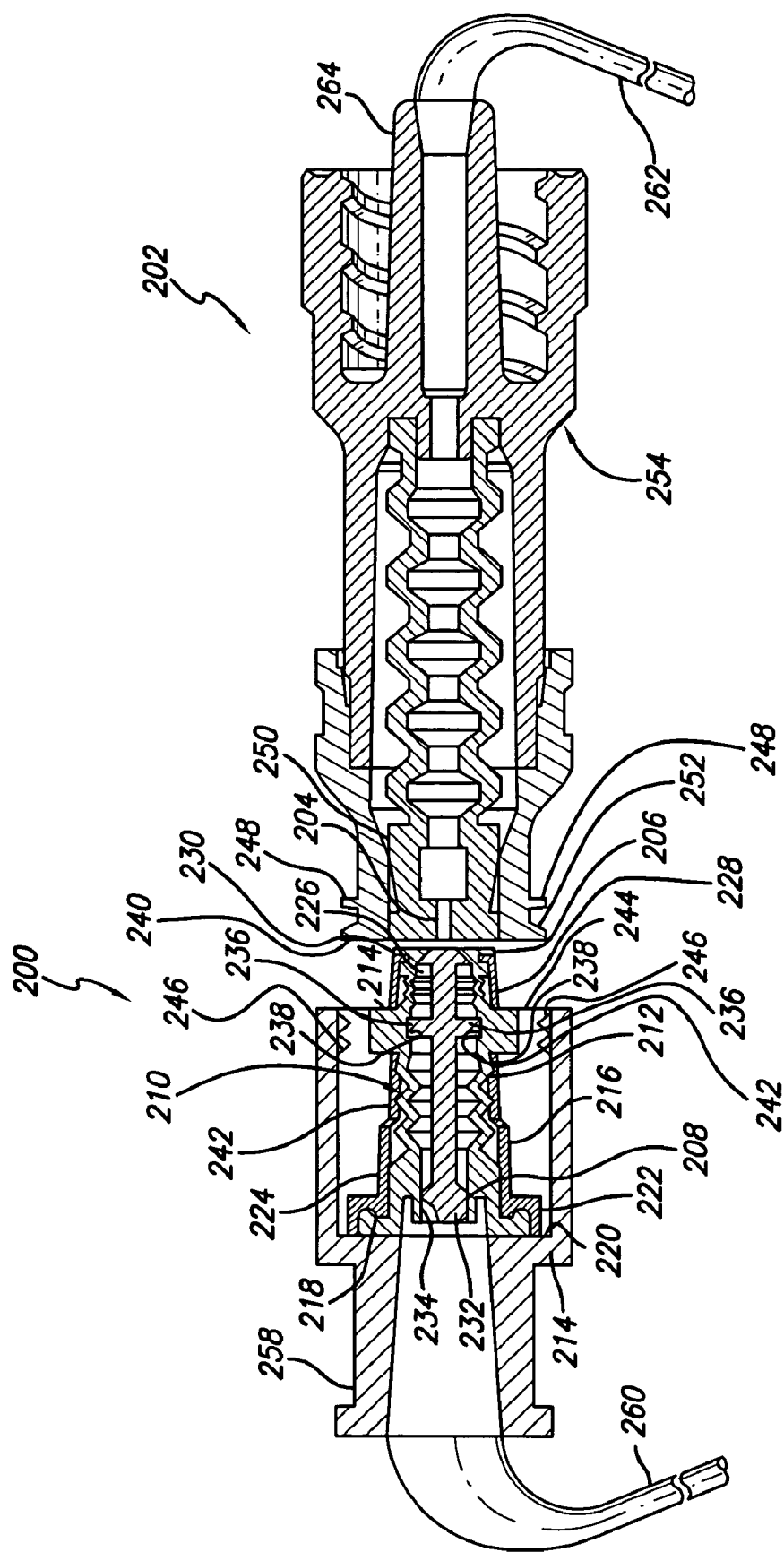
FIG. 29 is a side, cross-sectional view of the male connector of FIG. 28 showing it aligned with a compatible female valved connector prior to engagement.

FIG. 29 depicts the two luer connectors 200 and 202 just separated. In this position, a valve 204 in the female luer connector 202 is closed, and a first distal valve 206 and a second proximal valve 208 in the male luer connector 200 are closed. Flow through either connector is prevented because the respective valves are closed.

Reviewing the male connector 200 in more detail, the connector includes a resilient member 210 having an internal cavity 212. In FIG. 28, the resilient member is uncollapsed and the internal cavity has a first internal volume. The resilient member is mounted within a housing 214 and within a tubular projecting member 216. The base 218 of the resilient member is butted against the interior wall 220 of the housing and secured in place by the proximal end 222 of the tubular projecting member. An internal plug 224 is mounted within the resilient member. The plug includes a distal valve member 226 that mates with a valve seat 228 provided by the distal end 230 of the resilient member. The internal plug includes a proximal valve member 232 that mates with a proximal valve seat 234 provided by the resilient member, which in this embodiment, results in a type of poppet valve 208. The internal plug includes integral fins or radial flanges 236 that are inserted into radial pockets 238 formed in the resilient member. The resilient member provides a biasing force in the distal direction and tends to return itself and the internal plug to the configuration shown in FIG. 28 unless opposing forces in the proximal direction cause compression of the resilient member, as is discussed below.

Referring to both FIGS. 28 and 29, engagement of the male connector 200 with a female connector 202 causes the female connector's contact surface 240 to push the actuation surface 244 of the resilient member in the proximal direction, which causes the resilient member's contact surface 244, pockets 238, and the fins 236 and internal plug 224 to also move in the proximal direction. Upon the occurrence of enough proximal direction movement, the plug will disengage from the distal valve seat 228 thus opening the distal valve 206 and will disengage from the proximal valve seat 234 thus opening the proximal valve 208, as is described in more detail below. The tubular projecting member 216 includes slots 242 through which the actuation surface 244 of the resilient member projects so that it may contact the female connector contact surface 240. The tubular projecting member 216 is formed in the shape of a standard Luer in this embodiment, although other shapes are possible. The housing 214 may include internal threads 246 with which to engage threads 248 of the female connector for more secure locking of the two together.

The female connector 202 includes an internal piston 250 having an opening at its proximal end 252 that forms the female valve 204. As the piston is moved into the housing 254 of the female connector by a certain distance, it will open to thereby open the female valve and permit the flow of fluid through the female connector.

Figure 30:
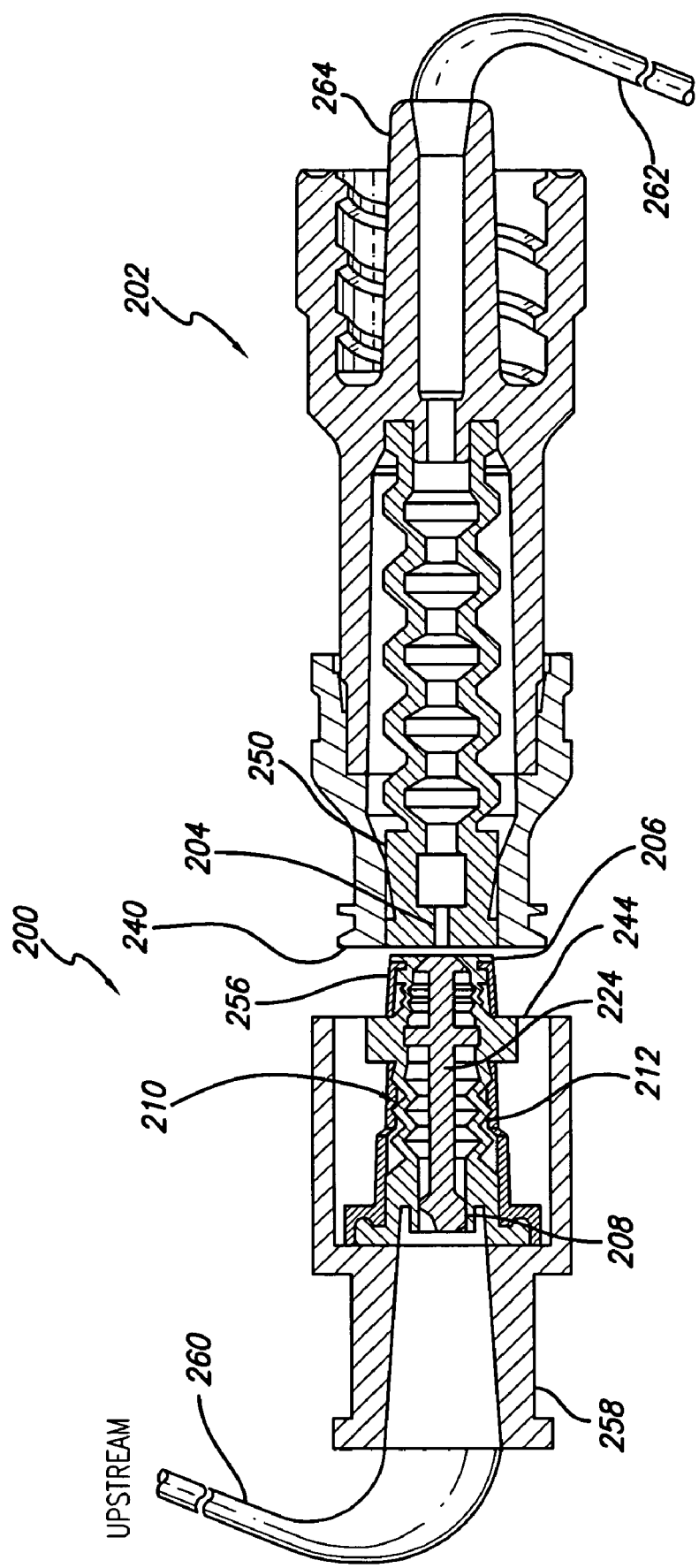
FIG. 30 is a view similar to FIG. 29 except that the male and female connectors have become partially engaged to the point where a distal valve of the male connector has opened while the proximal valve of the male connector and the valve of the female connector remain closed.

Turning now to FIG. 30, there is depicted the male 200 and female 202 connectors partially joined together. In this position, the forward contact surface 240 of the female luer connector has driven the actuation surface 244 of the male luer connector in the proximal direction far enough to open the first distal valve 206 while the second proximal valve 208 in the male connector remains closed. The cavity 212 of the resilient member in this position is now slightly collapsed and has an internal volume that is less than the first volume of the cavity shown in FIG. 28. The distal end 256 of the tubular projecting member or male luer portion 216 has driven the piston 250 of the female luer connector 202 a partial distance in the distal direction. The valve 204 of the female Luer connector is still closed, despite the displacement of the piston.

Thus in this FIG. 30, as the two connectors 200 and 202 are being engaged with one another, the distal valve 206 of the male connector has first opened while the proximal valve 208 of the male connector and the female connector valve 204 remain closed. This is due to the relative distances of movement and sizes of the various parts. The proximal valve seat 234 in the male connector resilient member 210 is designed to be long enough such that its valve 208 does not open until after the plug 224 has moved by a distance longer than the distance required to open the distal valve 206. The length of movement of the proximal valve required for opening is longer than the length of movement of the distal valve to achieve opening. Similarly, the distance of movement of the plug to open the distal valve of the male connector is selected to be less than the distance of movement of the piston 250 of the female connector that is required to open the female connector valve.

Figure 31:
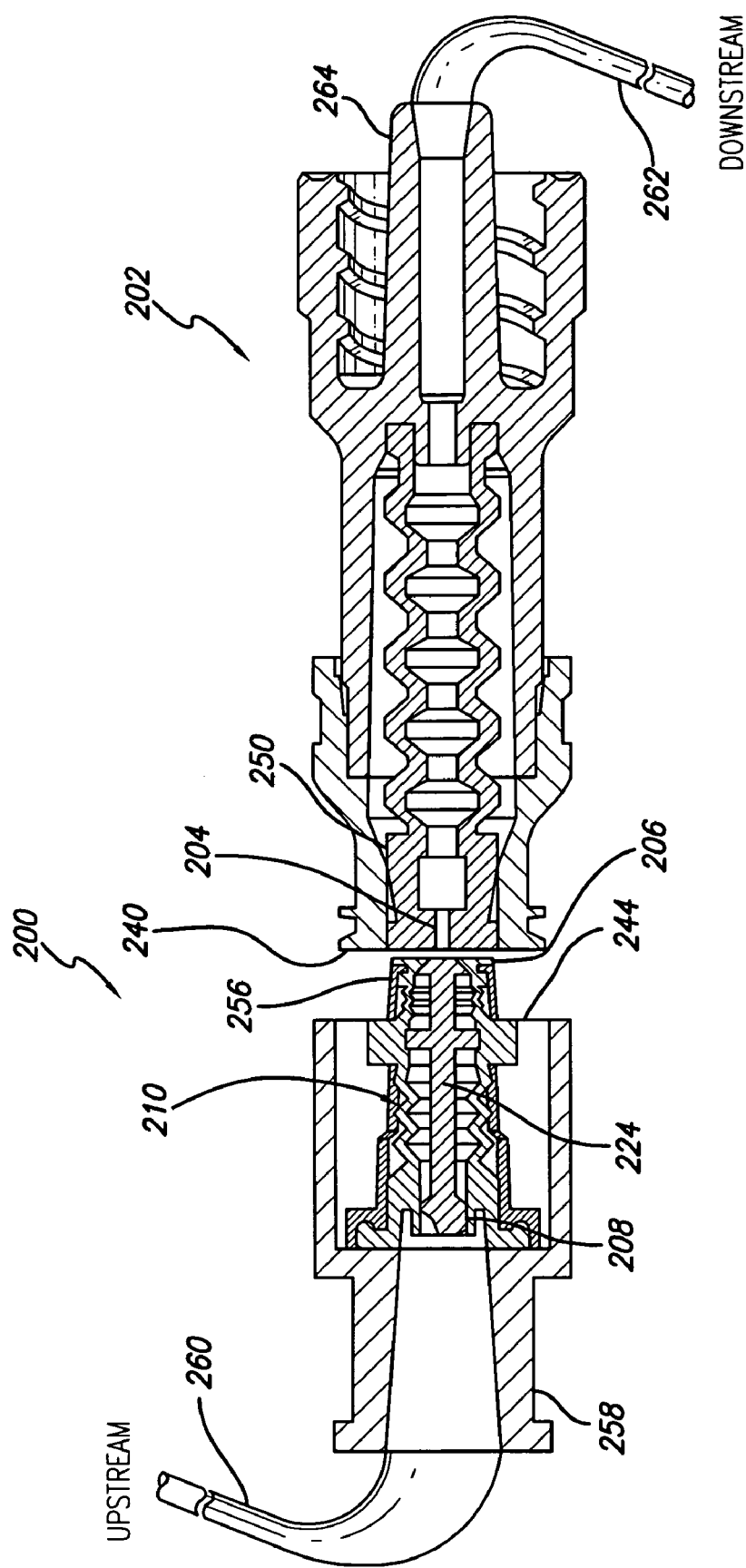
FIG. 31 is a view similar to FIG. 30 except that the male and female connectors have become further partially engaged to the point where the distal valve of the male connector has opened and the valve of the female connector has opened while the proximal valve of the male connector remains closed.

FIG. 31 depicts the male 200 and female 202 luer connectors further joined together than in FIG. 30. In this configuration, the distal end 256 of the male luer connector has driven the piston 250 of the female connector farther in the distal direction, so much so that the female connector valve 204 has now opened and fluid flow through the female connector may now occur. The contact surface 240 of the female connector has further driven the actuation surface 244 of the resilient member 210 further in the proximal direction further opening the distal valve 206; however, the proximal valve 208 is still closed. Thus, two valves of the three valves between the male and female connectors are now open. Fluid flow through the female connector can now occur but fluid flow through the male connector remains prevented due to the continuing closure of the proximal, or upstream, valve 208. As is apparent, the length of movement of the proximal valve required for opening is longer than the length of movement of the distal valve 206 of the male connector 200, and the length of movement to the female connector's valve 204 to achieve opening. Thus in this embodiment, the distance of movement of the internal plug 224 to open the distal valve of the male connector is selected to be less than the distance of movement of the piston 250 of the female connector that is required to open the female connector valve 204, yet more to open the proximal valve 208 than to open the female connector's valve.

Figure 32:
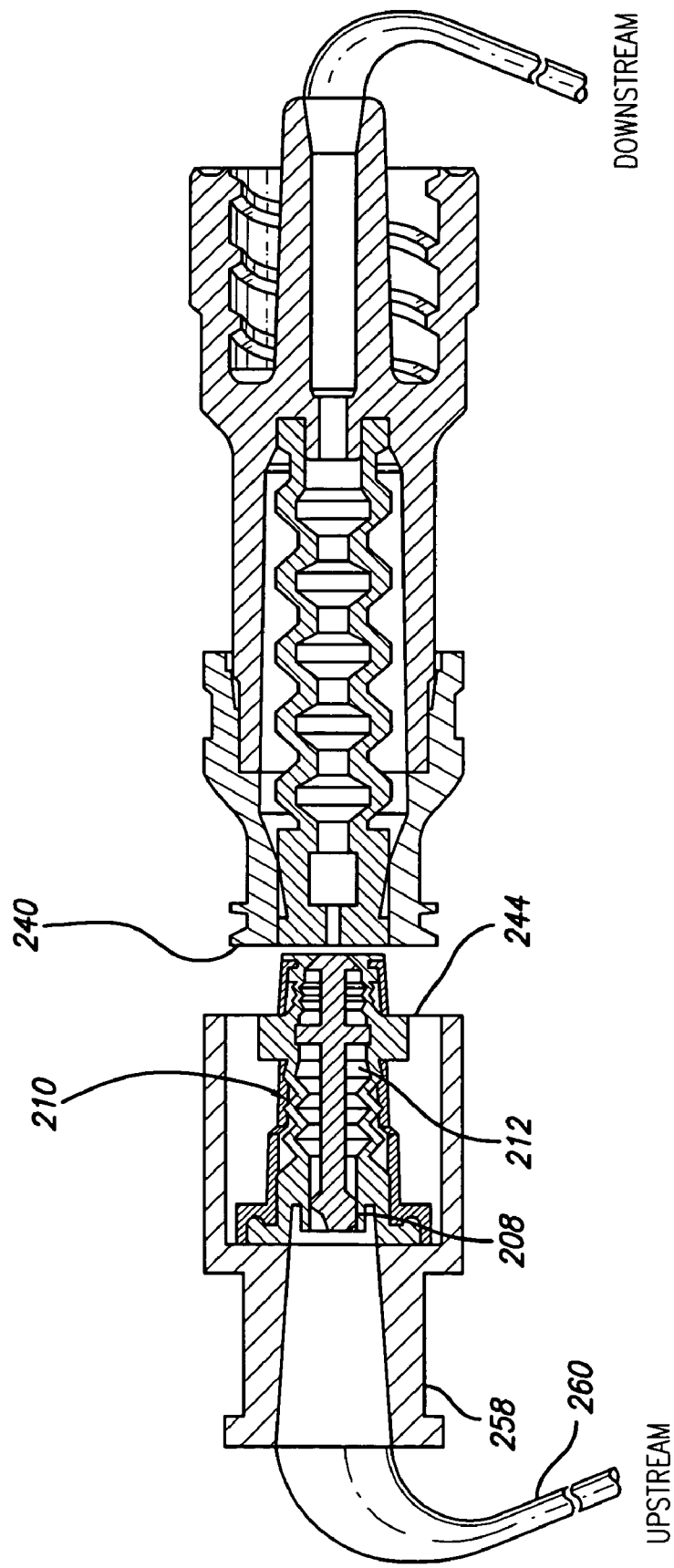
FIG. 32 is a view similar to FIG. 31 except that the male and female connectors have become fully engaged and both distal and proximal valves of the male connector are open and the valve of the female connector is also open for complete fluid flow through both connectors.

FIG. 32 depicts the complete operative engagement of the male 200 and female 202 Luer connectors such that all three depicted valves are open and fluid flow can occur between and through both connectors. In this configuration, the female connector contact surface 240 has driven the actuation surface 244 of the male connector far enough in the proximal direction to open the proximal valve 208. The compressible collapsible cavity 212 of the resilient member 210 is fully collapsed having now an even smaller internal volume that shown in the preceding FIGS. 28 through 31. Thus on engagement of the male connector having two valves, a distal or downstream valve and a proximal or upstream valve in accordance with aspects of the invention, with a female connector having an internal valve, the first valve that opens is the distal male connector valve. The second valve to open is the female connector valve, and the last valve to open is the proximal male connector valve. Fluid can now flow from the upstream line 260, through the male connector 200, through the female connector 202, and out through the downstream line 262. In this case, both upstream and downstream lines are shown as medical tubing, although other devices may be used. Additionally, the upstream connecting device 258 of the male connector 200 is shown as a Luer female connector but other types of coupling devices may be used. Similarly, the downstream coupling device 264 of the female connector 202 is shown as a male Luer connector but other types of coupling devices may be used.

Disengagement or disconnection of the male connector 200 and the female connector 202 from each other will result in a sequence of valve closure that is opposite the sequence of valve opening as discussed above. As just discussed in detail, the connectors are shown fully operatively engaged together in FIG. 32 and fluid flow through both valves can occur. A first stage of valve closure upon disengagement is shown in FIG. 31. As the separation of the male and female luer connectors begins, movement of the contact surface 240 of the female luer connector in the distal direction permits the actuation surface 244 of the resilient member 210 of the male Luer connector to also move in the distal direction due to the biasing force provided by the resilient member. As is shown in FIG. 31, the proximal valve 208 of the male connector has closed although the distal valve 206 of the male connector and the female connector valve 204 remain open. Thus, in the configuration of FIG. 31, the male connector is now closed to any fluid existing in an upstream line such as may be connected to the male connector's proximal female connector 258. The upstream line 260 is shown in exaggerated form in FIG. 31. In this configuration then, the internal components of the male connector, and consequently the female connector, are isolated from any upstream fluids.

FIG. 30 depicts the second stage of valve closure upon disconnection of the male connector 200 and female connector 202. As the separation of the male and female luer connectors further continues, the distal end of the male luer connector 256 has retreated moving in the proximal direction which has allowed the piston 250 of the female luer connector to resile also in the proximal direction thereby closing the female connector valve 204. Fluid flow through the female connector is now prevented. Thus both the male and female connectors are now isolated from any fluids in the upstream line 260 and in the downstream line 262.

As the male connector 200 moves from the configuration of FIG. 30 to the configuration of FIG. 29 during which the resilient member 210 moves in the distal direction to close the distal valve 206, a partial vacuum is created within the male connector. This is because the cavity 212 of the resilient member 210 is increasing in internal volume as the resilient member resiles to the configuration of FIG. 29 from the configuration of FIG. 30. As soon as the internal volume of the resilient member begins increasing, a partial vacuum forms which may be used to draw fluid into the male connector. By proper sequencing of the valves of the connector in conjunction with each other and with the valve of the female connector, the force of this partial vacuum is directed to the interface between the male connector and the female connector 202 to thereby draw fluid residing on that interface into the male connector.

Because the valves have been sequenced so that the only valve remaining open at this time is the distal valve 206 of the male connector, the existence of this partial vacuum will draw any fluid remaining at the interface between the two connectors 200 and 202 and on the distal tip or end 230 of the resilient member 210 into the male connector before the distal valve 206 closes. As the connectors are further separated, the cavity 212 of the resilient member further expands, drawing more fluid from the interface of the two connectors, until the distal valve 206 eventually closes as is shown in the configuration of FIG. 29. Thus in the configuration of FIG. 29, both the upstream line 260, having the male connector 200 at its distal end, and the downstream line 262, having the female connector 202 at its proximal end, are sealed by the respective connectors, each of which has at least one internal valve to isolate the line. In the case of isolation of the upstream line 260, the male connector 200 will seal the distal end of the line, and even withdraws excess fluid from the distal end of the connector upon disengagement or disconnection from the female connector 202. This is an especially useful feature in the case where caustic fluids may have been conducted by the upstream line and some of that fluid may have reached surfaces at the interface between the female and male connectors. If these connectors were fully separated and such caustic fluid remained on their surfaces, that caustic fluid may be transferred to the clinician handling the connectors. Such fluids may cause injury to health care workers and patients if applied to skin surfaces thus their containment in the upstream line by means of this vacuum, draw-back feature is especially useful.

Although shown with tubing 260 and 262 at the ends of the connectors in FIGS. 28 through 32, this is for example purposes only and is not meant to be restrictive. Various conductive, container, or other components may be used in place of the tubing shown. For example, the male connector 200 may form the nozzle end of a syringe instead of being connected to tubing. The female connector 202 may form part of a vial adapter or vial access device so that liquid from the syringe connected to the male connector may be injected into a vial of medical substance, mixed and then withdrawn back into the syringe, as an example. Other applications are possible.

The various embodiments of the male luer described above provide for automatic sealing of the end opening in the male luer as the male and female luers are disconnected, reducing the risk of an operator coming into contact with the potentially hazardous fluid flowing through the connector.

Although some exemplary embodiments of the invention have been described above by way of example only, it will be understood by those skilled in the field that modifications may be made to the disclosed embodiments without departing from the scope of the invention, which is defined by the appended claims.

What is claimed is:

1. A male Luer connector for connection with a female Luer connector for medical fluid flow, the female connector having a front contact surface and an internal valve, the male Luer connector comprising:
   a tubular housing having a distal end and a proximal end, the distal end configured to engage the female Luer connector and establish an interface; and
   vacuum means for creating a partial vacuum at the distal end of the tubular housing during disengagement of the male connector from the female connector during a time period when the female valve is closed;
   whereby the vacuum means draws fluid residing at the interface away from the interface during disengagement of the male and female connectors.

2. The male Luer connector of claim 1 wherein the vacuum means is located within the tubular housing.

3. The male Luer connector of claim 1 wherein the vacuum means comprises a first valve controlling the flow of fluid through the proximal end of the tubular housing.

4. The male Luer connector of claim 1 wherein the vacuum means comprises a second valve controlling the flow of fluid through the distal end of the tubular housing.

5. The male Luer connector of claim 1 wherein:
   the vacuum means comprises a first valve controlling the flow of fluid through the proximal end of the tubular housing;
   the vacuum means comprises a second valve controlling the flow of fluid through the distal end of the tubular housing; and
   the vacuum means is also for controlling the second valve to remain open while the vacuum means creates the partial vacuum.

6. The male Luer connector of claim 5 wherein the vacuum means is also for controlling the first valve to close first, and controlling the second valve to remain open after the female connector valve closes during disengagement of the female connector from the male connector.

7. The male Luer connector of claim 5 wherein:
   the vacuum means comprises an actuator that controls the opening and closing of the first and second valves;
   the vacuum means further comprises an actuation surface disposed so as to be moveable by the front contact surface of the female connector to control the actuator to open and close the first and second valves.

8. The male Luer connector of claim 7 wherein:
   the first valve comprises a proximal valve disposed at the proximal end of the tubular housing;
   the second valve comprises a distal valve disposed at the distal end of the tubular housing; and the actuator is disposed within the tubular housing to open and close both the proximal and distal valves.

9. The male Luer connector of claim 8 wherein the vacuum means further comprises a resilient member disposed to bias the actuator to close both the proximal and distal valves.

10. The male Luer connector of claim 9 wherein the resilient member has an inner variable-volume cavity through which fluid flows, the cavity having a first volume when the proximal and distal valves are closed, the cavity having a second volume smaller than the first volume when the distal valve is open;

whereby the resilient member creates a partial vacuum when moving from the second volume to the first volume during closure of the distal valve.

11. The male Luer connector of claim 10 wherein:
the cavity has the second volume when the male and female connectors are engaged; and
the cavity moves to the first volume thereby creating the partial vacuum when the male and female connectors are being disengaged.

12. The male Luer connector of claim 11 wherein:
the resilient member forms a valve seat for the distal valve and a valve seat for the proximal valve;
the actuator provides a distal valve member for the distal valve that fits into the distal valve seat to close the distal valve and provides a proximal valve member for the proximal valve that fits into the proximal valve seat to close the proximal valve.

13. The male Luer connector of claim 12 wherein:
the resilient member provides the actuation surface;
the actuator is disposed within the resilient member in contact with the resilient member;
movement of the resilient member due to engagement with the front contact surface of the female connector causes corresponding movement of the actuator to open and close the distal and proximal valves.

14. A male connector for connection with a female connector to establish a path for medical fluid flow, the female connector having a front contact surface and an internal valve, the male connector comprising:

a tubular housing having a distal end and a proximal end, the distal end configured to engage the female Luer connector and establish an interface;
a first valve seat disposed for use in controlling the flow of fluid through the distal end of the tubular housing;
an internal plug disposed within the tubular housing, the internal plug having a first valve member that engages the first valve seat to prevent the flow of fluid past the first valve seat; and
a resilient member disposed within the tubular housing so as to bias the internal plug to engage the first valve seat, the resilient member having an inner variable-volume cavity through which fluid flows, the cavity having a first volume when the first valve is closed, the cavity having a second volume smaller than the first volume when the first valve is open;
wherein the resilient member is disposed so that engagement of the female connector with the male connector causes the resilient member cavity to move to the second volume and disengagement of the female connector from the male connector causes the cavity to move from the second volume to the first volume thereby creating a partial vacuum.

15. The male connector of claim 14 wherein the first valve seat is disposed at the proximal end of the housing;
whereby moving the resilient member cavity from the second volume to the first volume creates the partial vacuum at the distal end of the tubular housing to draw away medical fluid existing at an interface between the male and female connectors during disengagement.

16. The male connector of claim 15 wherein the resilient member is disposed so that the cavity moves to the first volume during a time period after the valve of the female connector has closed whereby the partial vacuum draws away medical fluid existing at an interface between the male and female connectors during disengagement.

17. The male connector of claim 16 wherein the first valve seat is a distal valve seat disposed for use in controlling the flow of fluid through the distal end of the tubular housing;
the male connector further comprising a proximal valve seat disposed for use in controlling the flow of fluid through the proximal end of the tubular housing;
wherein the first valve member is a distal valve member that engages the distal valve seat to prevent the flow of fluid past the distal valve seat, and further comprising a proximal valve member that engages the proximal valve seat to prevent the flow of fluid past the proximal valve seat; and
wherein the resilient member biases the internal plug to engage both the distal valve seat and the proximal valve seat, the first volume of the cavity existing when the proximal and distal valves are closed, the second volume of the cavity existing when the distal valve is open.

18. A method for disengaging a male connector from a female connector, the male connector including a distal end engaged with the female connector, a proximal end, and an internal valve and the female connector including a proximal end engaged with the male connector, a distal end, and an internal valve, the method comprising:

closing a first valve in the male connector at the proximal end of the male connector to isolate an interface between the male connector and the female connector from fluid at the proximal end of the male connector; and
creating a partial vacuum at the interface of the male connector and female connector to draw fluid at the interface away from the interface.

19. The method of claim 18 further comprising the step of closing the internal valve of the female connector before the step of creating a partial vacuum.

20. The method of claim 19 further comprising the step of closing a valve at the distal end of the male connector after the step of creating a partial vacuum.

21. The method of claim 19 wherein the step of creating a partial vacuum comprises creating a partial vacuum within the male connector and drawing fluid at the interface into the male connector.

* * * * *

UNITED STATES PATENT AND TRADEMARK OFFICE
CERTIFICATE OF CORRECTION

PATENT NO. : 7,044,441 B2  Page 1 of 1
APPLICATION NO. : 11/010096
DATED : May 16, 2006
INVENTOR(S) : Mark C. Doyle It is certified that error appears in the above-identified patent and that said Letters Patent is hereby corrected as shown below:

Column 1,
Line 45, after "an amount", insert --escaping from the connectors, it can still be significant enough to cause harm to any person exposed--.

Column 9,
Line 63, delete "has a integral" and insert --has integral--.

Signed and Sealed this

Fourteenth Day of November, 2006

JON W. DUDAS
*Director of the United States Patent and Trademark Office*